(12) United States Patent
Iibuchi et al.

(10) Patent No.: US 10,842,942 B2
(45) Date of Patent: Nov. 24, 2020

(54) LIQUID MEDICINE ADMINISTRATION DEVICE

(71) Applicant: TERUMO KABUSHIKI KAISHA, Tokyo (JP)

(72) Inventors: Ruriko Iibuchi, Kanagawa (JP); Manabu Arinobe, Kanagawa (JP); Taeko Masuda, Kanagawa (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 187 days.

(21) Appl. No.: 16/147,016

(22) Filed: Sep. 28, 2018

(65) Prior Publication Data
US 2019/0030255 A1 Jan. 31, 2019

Related U.S. Application Data

(63) Continuation of application No. PCT/JP2017/012786, filed on Mar. 29, 2017.

(30) Foreign Application Priority Data

Mar. 30, 2016 (JP) ................................. 2016-067928

(51) Int. Cl.
*A61M 5/315* (2006.01)
*A61M 5/145* (2006.01)
*A61M 5/158* (2006.01)
*A61M 5/172* (2006.01)

(52) U.S. Cl.
CPC ...... *A61M 5/31528* (2013.01); *A61M 5/1452* (2013.01); *A61M 5/31513* (2013.01); *A61M 5/31583* (2013.01); *A61M 5/172* (2013.01); *A61M 2005/14506* (2013.01); *A61M 2005/1581* (2013.01); *A61M 2005/3152* (2013.01); *A61M 2005/31518* (2013.01);
(Continued)

(58) Field of Classification Search
CPC ...... A61M 2005/31518; A61M 5/1452; A61M 2005/3152; A61M 5/31598; F16H 25/2056
See application file for complete search history.

(56) References Cited

U.S. PATENT DOCUMENTS 7,066,909 B1 6/2006 Peter et al.

FOREIGN PATENT DOCUMENTS

JP 2008-125803 A 6/2008
WO WO-2013/148270 A1 10/2013

OTHER PUBLICATIONS

International Search Report and Written Opinion in PCT/JP2017/012786, dated Jul. 4, 2017, 6 pages.

*Primary Examiner* — Emily L Schmidt
(74) *Attorney, Agent, or Firm* — Foley & Lardner LLP

(57) ABSTRACT

A drug solution injection device is provided with a barrel, a gasket, and a plunger mechanism. The plunger mechanism is provided with a rotation member, a first moving member, and a second moving member. The plunger mechanism is configured to perform a first extension operation and a second extension operation. In the first extension operation, the first moving member advances to a predetermined position with respect to the rotation member and the second moving member in conjunction with rotation of the rotation member. In the second extension operation, the second moving member advances with respect to the rotation member together with the first moving member after the first extension operation, in conjunction with rotation of the rotation member.

9 Claims, 25 Drawing Sheets

(52) U.S. Cl.
CPC ............. *A61M 2005/31588* (2013.01); *A61M 2205/103* (2013.01); *A61M 2205/8206* (2013.01)

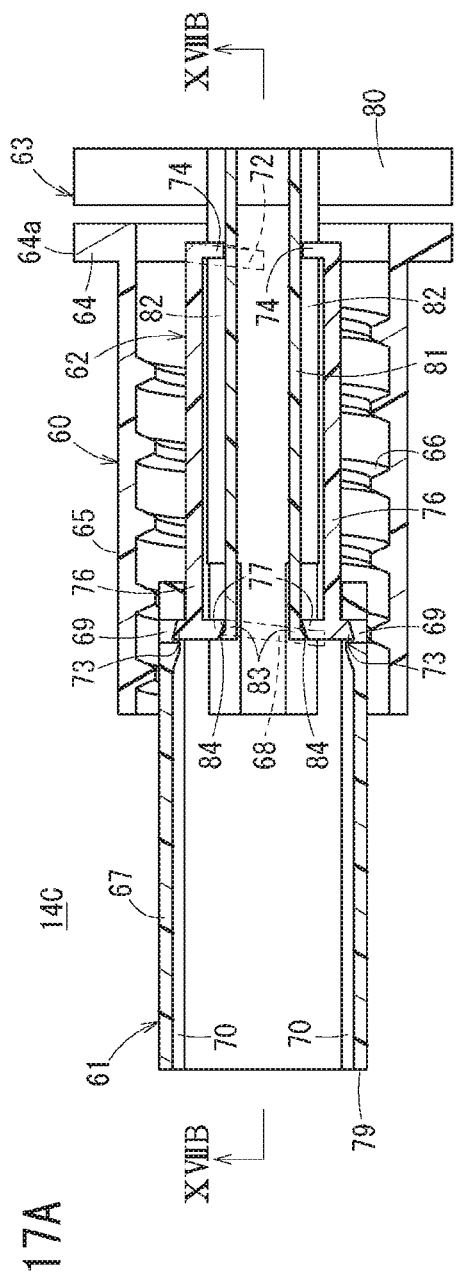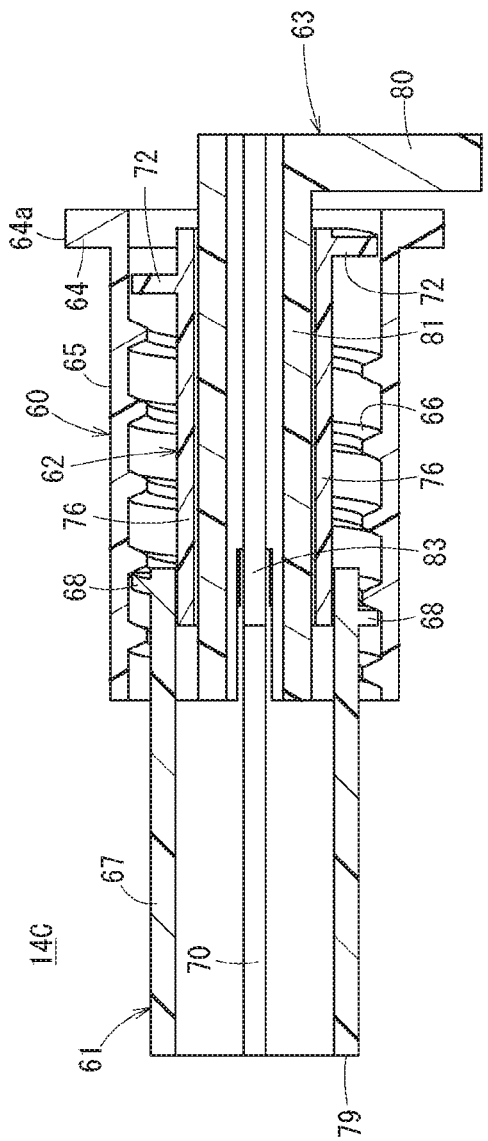

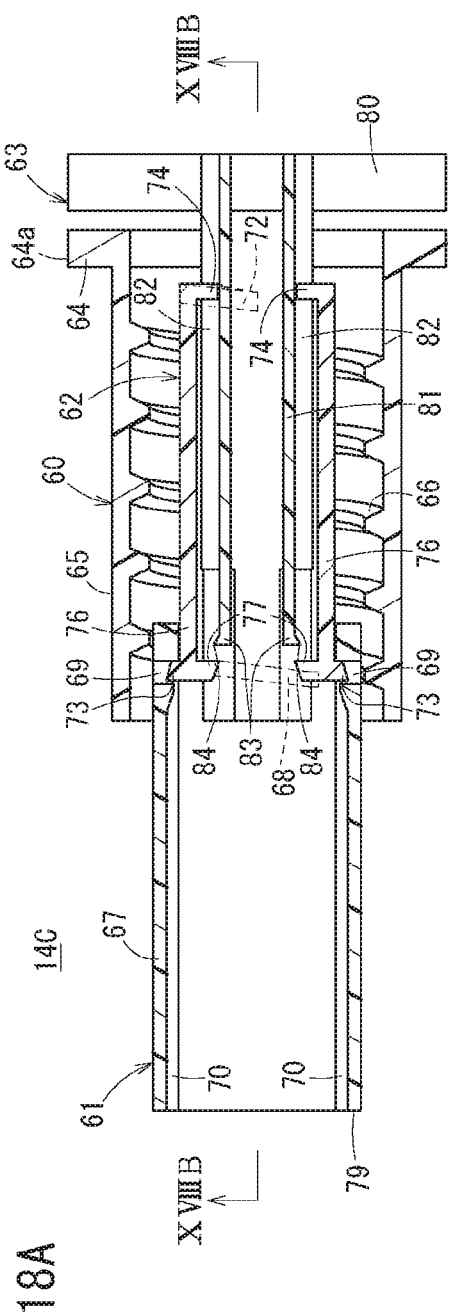
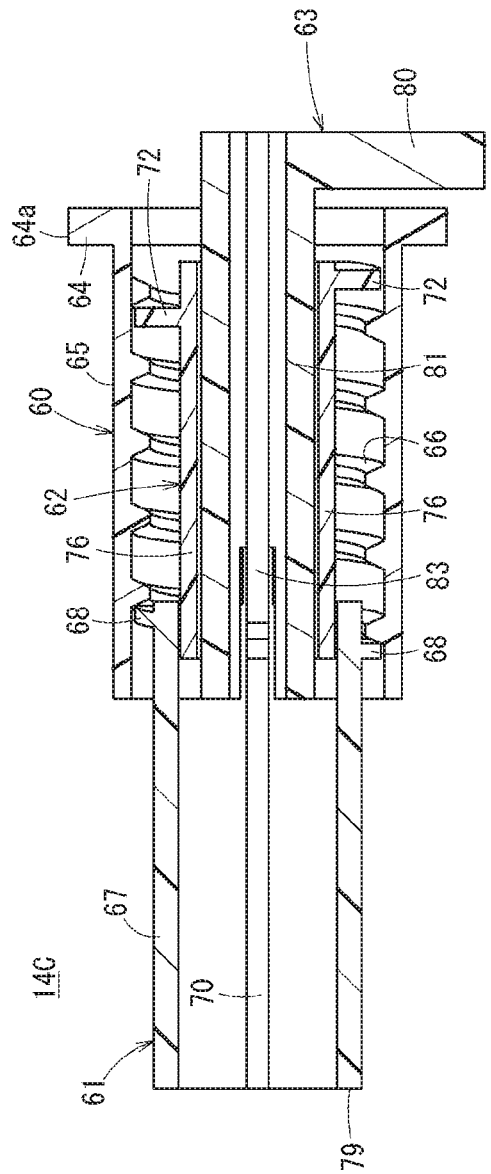
FIG. 18A
FIG. 18B

LIQUID MEDICINE ADMINISTRATION DEVICE

CROSS-REFERENCE TO RELATED APPLICATIONS

The present application is a bypass continuation of PCT Appl. No. PCT/JP2017/012786, filed on Mar. 29, 2017, which claims priority to Japanese Appl. No. 2016-067928, filed on Mar. 30, 2016. The contents of these applications are hereby incorporated by reference in their entireties.

BACKGROUND

The present disclosure relates to a drug solution injection device for injecting a drug solution filled in a barrel into a living body under a pressing action of a plunger.

In the related art, a syringe pump-type drug solution injection device is known that administers a drug solution filled in a barrel into a living body under a pressing action of a plunger. Also known with regard to this type of drug solution injection device is a mechanism (hereinafter, referred to as "the plunger mechanism according to the related art") in which a plunger and a screw shaft are screwed together and the plunger is allowed to advance under a rotation action of the screw shaft as disclosed in, for example, WO 2013/148270 A.

SUMMARY

In recent years, drug solution injection devices are becoming more compact, and body-affixed drug solution injection devices have appeared as well. Body-affixed drug solution injection devices, in particular, need to be as small in size as possible in the interest of usability and for affixable area-related limitations. In the plunger mechanism according to the related art, the single plunger advances with respect to the screw shaft, and thus the effect of reducing the size of the drug solution injection device is insufficient.

Embodiments of the present disclosure have been developed in view of these problems, and an object of certain embodiments is to provide a drug solution injection device that can be reduced in size in a more effective manner.

According to one embodiment, a drug solution injection device for injecting a drug solution into a living body includes: a barrel filled with the drug solution; a gasket slidably disposed in the barrel; and a plunger mechanism that is configured to extend in an axial direction and to push out the drug solution from the barrel by pressing the gasket as the plunger mechanism extends, wherein the plunger mechanism comprises: a rotatable rotation member including a screw portion; a first moving member including a first projection portion that is configured to engage with the screw portion, and a pressing portion that is configured to press the gasket, the first moving member being configured to be displaced in the axial direction with respect to the rotation member; and a second moving member including a second projection portion that is configured to engage with the screw portion, the second moving member being configured to be displaced in the axial direction with respect to the rotation member, wherein, in an initial state in which the drug solution is yet to be pushed out, the rotation member, the first moving member, and the second moving member are configured to be disposed at positions overlapping each other in the axial direction, the screw portion and the first projection portion are configured to be engaged with each other, and the screw portion and the second projection portion are configured not to be engaged, and wherein an extension operation of the plunger mechanism comprises: a first extension operation in which the first moving member is configured to advance to a predetermined position with respect to the rotation member and the second moving member under an engagement action of the screw portion and the first projection portion as the rotation member rotates from the initial state; and a second extension operation in which the second moving member is configured to advance with respect to the rotation member together with the first moving member under an engagement action of the screw portion and the second projection portion after the first extension operation in conjunction with a rotation of the rotation member.

In the drug solution injection device configured as described above, the plunger mechanism extends over a plurality of stages, and thus it is possible to shorten the plunger mechanism and the drug solution injection device can be reduced in size to the same extent. In the case of adhering to the surface of a patient's body, the area that is required for adhering can be reduced from the device size reduction, and thus embodiments of the present disclosure can be easily applied to applications such as adhering to the surface of a patient's body as well. Further, the device size reduction can lead to usability improvement in terms of portability, storage, and soon. Further, in a case where the gasket is pushed with a spring, air, or the like, it is difficult to control the speed at which the drug solution is injected in a constant manner. However, with the drug solution injection device according to embodiments of the present disclosure, the drug solution can be injected at a constant speed because an engagement structure mechanically moves a movable portion (first moving member and second moving member).

In one aspect, the first moving member may comprise a first engagement portion; the second moving member may comprise a second engagement portion configured to be engage with the first engagement portion; and when the first moving member has advanced to the predetermined position with respect to the second moving member, the first engagement portion and the second engagement portion is configured to be engaged with each other such that axial displacement of the first moving member relative to the second moving member is restricted.

With this configuration, the second moving member is capable of causing the first moving member to advance in a reliable manner when the second moving member advances with respect to the rotation member.

In one aspect, the screw portion and the first projection portion may be configured to be disengaged after the screw portion and the second projection portion are engaged with each other in conjunction with a rotation of the rotation member during the second extension operation.

With this configuration, the engagement opponent of the screw portion can be timely changed from the first projection portion to the second projection portion, and thus a transition from the first extension operation to the second extension operation can be smoothly performed.

In one aspect, one of the first engagement portion and the second engagement portion may be an elastically supported claw portion; and the other of the first engagement portion and the second engagement portion may be an engagement groove portion with which the claw portion is configured to engage.

With this configuration, the first engagement portion and the second engagement portion can be quickly engaged at a point in time when the first moving member has advanced to the maximum with respect to the second moving member, and thus the first moving member can be swiftly locked with respect to the second moving member through a linear movement alone.

In one aspect, one of the first moving member and the second moving member may include a guide groove extending along the axial direction of the plunger mechanism; the engagement portion provided in the other of the first moving member and the second moving member among the first engagement portion and the second engagement portion may be a projecting portion that protrudes from an outer surface or an inner surface of the other member and that is configured to be inserted into the guide groove in the initial state; the engagement portion provided in the one of the first engagement portion and the second engagement portion may be a lock groove that is shorter than the guide groove and that is configured to allow the projecting portion to be engaged therewith, a movement of the first moving member in a proximal end direction relative to the second moving member may be configured to be restricted by engagement between the lock groove and the projecting portion, and the lock groove may be disposed at a different circumferential position from the guide groove in the one of the moving members; one end of the guide groove and one end of the lock groove may communicate with each other via a relay groove; and a lock operation, which restricts the movement of the first moving member in the proximal end direction relative to the second moving member in the plunger mechanism, may include: a rotation operation in which the first moving member is configured to rotate with respect to the second moving member after the projecting portion relatively moves in the axial direction with respect to the guide groove in conjunction with an advance of the first moving member with respect to the second moving member, such that the projecting portion relatively moves in the relay groove toward the lock groove; and a locking operation in which the second moving member is configured to advance with respect to the first moving member after the rotation operation, such that the projecting portion enters the lock groove and the projecting portion is locked in the lock groove.

With this configuration, it is possible to structurally stabilize the mechanism portion that locks the first moving member with respect to the second moving member.

In one aspect, the screw portion may have a form of a male screw; the first moving member may be formed of a hollow tubular body including a first lumen, the first projection portion may protrude toward an inside of the first moving member, and the male screw may be configured to be inserted in the first lumen in the initial state; and the second moving member may be formed of a hollow tubular body including a second lumen, the second projection portion may protrude toward an inside of the second moving member, and the male screw and the first moving member may be configured to be inserted in the second lumen.

With this configuration, the outer diameter size of the plunger mechanism can be reduced with ease.

In one aspect, the rotation member may be formed of a hollow tubular body including a lumen and the screw portion may have a form of a female screw formed in an inner peripheral portion of the rotation member; the first moving member may be formed of a hollow tubular body including a first lumen, the first projection portion may protrude toward an outside of the first moving member, and the first moving member may be configured to be inserted in the lumen in the initial state; and the second projection portion may protrude toward an outside of the second moving member and the second moving member may be configured to be inserted in the first lumen.

A mechanism in which the second moving member advances after the first moving member advances can be realized also with the configuration in which the first moving member is disposed inside the rotation member and the second moving member is disposed inside the first moving member as described above.

In one aspect, the drug solution injection device further includes a support member that is configured to guide the second moving member in the axial direction while restricting rotation of the second moving member, wherein the second moving member may include a guide portion that is configured to guide the first moving member in the axial direction while restricting rotation of the first moving member.

With this configuration, it is possible to prevent the first moving member and the second moving member from rotating along with rotation of the rotation member, and thus the rotation operation of the rotation member can be appropriately converted into the axial operations of the first moving member and the second moving member.

In one aspect, the drug solution injection device further includes a support member that is configured to guide the second moving member in the axial direction, wherein the support member and the second moving member may be configured to engage with each other such that the position of the second moving member with respect to the rotation member is maintained until termination of the first extension operation; and the rotation member is configured to rotate, with the screw portion and the first projection portion engaged with each other, such that the support member and the second moving member are disengaged.

With this configuration, it is possible to prevent the second moving member from advancing by being pulled by the advancing of the first moving member during the first extension operation.

With the drug solution injection device according to certain embodiments described in the present disclosure, device size reduction can be achieved in a more effective manner.

BRIEF DESCRIPTION OF THE DRAWINGS

FIG. 17A is a cross-sectional view of a state in which the second moving member has further and slightly advanced from the state illustrated in FIG. 16, and FIG. 17B is a cross-sectional view taken along line XVIIB-XVIIB of FIG. 17A.

FIG. 18A is a cross-sectional view of a state in which the second moving member has further and slightly advanced from the state illustrated in FIG. 17A, and FIG. 18B is a cross-sectional view taken along line XVIIIB-XVIIIB of FIG. 18A.

DETAILED DESCRIPTION

Embodiments of a drug solution injection device will be described below with reference to accompanying drawings.

Figure 1:
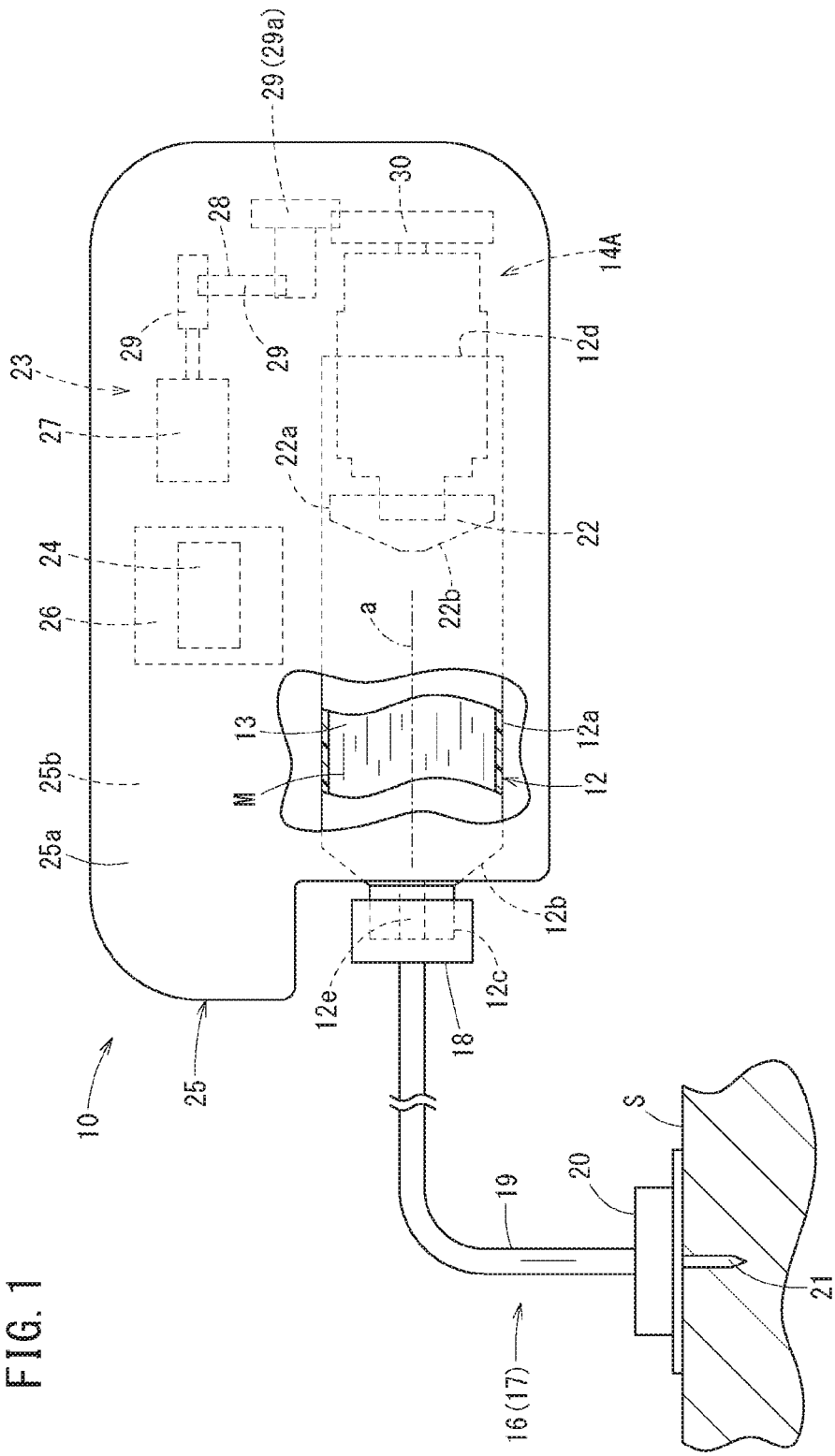
FIG. 1 is an external view of a drug solution injection device according to one embodiment.

A drug solution injection device 10 according to the embodiment illustrated in FIG. 1 is used for injecting a drug solution M into a living body. The drug solution injection device 10 continuously administers the drug solution M filled in a barrel 12 into a living body under a pressing action of a plunger mechanism 14A over a relatively long time (such as approximately several minutes to several hours). The drug solution injection device 10 may intermittently administer the drug solution M into a living body as well.

Examples of the drug solution M include a protein preparation, a narcotic analgesic, and a diuretic.

As illustrated in FIG. 1, when the drug solution injection device 10 is used, a patch-type needle-attached tube 17 or the like is connected to the drug solution injection device 10 as an injection line 16 and the drug solution M discharged from the barrel 12 is injected into a patient's body via the needle-attached tube 17. The needle-attached tube 17 is provided with a connector 18 connectable to a tip portion 12c of the barrel 12 provided with a discharge port 12e, a flexible liquid transfer tube 19 having one end portion connected to the connector 18, a patch portion 20 connected to the other end of the liquid transfer tube 19 and affixable to a skin S, and a needle 21 protruding from the patch portion 20. The needle 21 substantially perpendicularly punctures the skin S. Note that the needle 21 may obliquely puncture the skin S as well.

Incidentally, the injection line 16 connected to the drug solution injection device 10 is not limited to the patch-type needle-attached tube 17 described above. For example, a puncture needle (such as a winged needle) may be connected to the tip of the liquid transfer tube 19 in the injection line 16. Alternatively, the injection line 16 may be a bent needle connectable to the tip portion 12c of the barrel 12 without passing through the liquid transfer tube 19. In this case, the bent needle is bent by, for example, approximately 90° downwards from the tip portion 12c of the barrel 12 and perpendicularly punctures the skin S in conjunction with affixing (adhering) of the drug solution injection device 10 to the skin S. In addition, a part of the needle and the injection line and the tip portion 12c of the barrel 12 may be inside the barrel 12, and the tip of the needle may protrude more than the barrel 12. Even in this case, the needle perpendicularly punctures the skin S in conjunction with affixing (adhering) of the drug solution injection device 10 to the skin S.

The drug solution injection device 10 is provided with the barrel 12 filled with the drug solution M, a gasket 22 slidably disposed in the barrel 12, the plunger mechanism 14A connected to the gasket 22, a drive unit 23 that drives the plunger mechanism 14A, a battery 26 that supplies electric power necessary for operating the drug solution injection device 10, a control unit 24 that controls the drive unit 23, and a housing 25 that accommodates the barrel 12, the gasket 22, the plunger mechanism 14A, the drive unit 23, the battery 26, and the control unit 24.

The barrel 12 is formed in a hollow cylindrical shape and has a drug solution chamber 13 therein. Specifically, the barrel 12 has a body portion 12a having constant inner and outer diameters in the axial direction thereof, a shoulder portion 12b having inner and outer diameters reduced in a tapered shape from the tip of the body portion 12a in the tip direction, and the tip portion 12c protruding in the tip direction from the shoulder portion 12b. A proximal end opening 12d is formed at the proximal end of the body portion 12a. The discharge port 12e communicating with the drug solution chamber 13 is formed in the tip portion 12c. The barrel 12 is filled with the drug solution M in advance.

The gasket 22 is made of an elastic resin material such as a rubber material and an elastomer material. The outer peripheral portion thereof is in close contact with the inner peripheral surface of the barrel 12 (body portion 12a) in a liquid-tight manner. As a result, the proximal end side of the drug solution chamber 13 is closed in a liquid-tight manner. The gasket 22 has a base portion 22a that has an outer peripheral surface that is in close contact with the body portion 12a of the barrel 12 in a liquid-tight manner and a cone portion 22b that protrudes in the tip direction from the base portion 22a and has an outer diameter reduced in a tapered shape in the tip direction as in the case of the shoulder portion 12b of the barrel 12. In the initial state of the drug solution injection device 10 illustrated in FIG. 1, the gasket 22 is positioned closer to the tip side than the proximal end of the barrel 12.

The plunger mechanism 14A is capable of extending in the axial direction under the drive action of the drive unit 23. The plunger mechanism 14A is configured to cause the gasket 22 connected to the tip portion thereof to advance in the barrel 12 and push out the drug solution M from the barrel 12 as the plunger mechanism 14A extends. In the initial state of the drug solution injection device 10, the tip side of the plunger mechanism 14A is inserted in the proximal end side of the barrel 12 and the proximal end side of the plunger mechanism 14A protrudes in the proximal end direction from the proximal end opening 12d of the barrel 12. In other words, the proximal end side of the plunger mechanism 14A is exposed to the outside of the barrel 12. Note that details of the plunger mechanism 14A will be described later.

The drive unit 23 has a motor 27 driven and controlled under the control action of the control unit 24 with the battery 26 serving as an electric power source and a power transmission unit 28 decelerating the rotation of the motor 27 and transmitting the rotation to a rotation member 30 of the plunger mechanism 14A (described later). The power transmission unit 28 is a gear mechanism that has a plurality of gears 29. The plurality of gears 29 has an output gear 29a. The output gear 29a meshes with the rotation member 30 of the plunger mechanism 14A. The control unit 24 is capable of controlling the motor 27 such that the plunger mechanism 14A extends at a predetermined constant speed. As a result, the drug solution M in the barrel 12 can be injected into a living body at a constant speed.

The housing 25 is a hollow member configured to accommodate the barrel 12, the gasket 22, the plunger mechanism 14A, the drive unit 23, the battery 26, and the control unit 24. The tip portion 12c of the barrel 12 protrudes from the housing 25 and is exposed to the outside. The housing 25 has an upper surface 25a and a bottom surface 25b. The drug solution injection device 10 can be configured as, for example, a patch-type device used after being adhered to the skin S of a patient. In a case where the drug solution injection device 10 is a patch-type device, a sheet-shaped affixing portion (adhesive portion) affixable to the skin S is provided on the bottom surface 25b of the housing 25. A peelable protective sheet is adhered on the affixing surface of the affixing portion in the initial state of the drug solution injection device 10.

The drug solution injection device 10 may be configured as a device in which a mounting tool such as a hook and a clip is provided on the back surface of the housing 25 and is attached by hooking or the like onto a patient's clothes (such as the waist part of his or her pants). Further, the barrel 12 filled with the drug solution M, the gasket 22 slidably disposed in the barrel 12, and the plunger mechanism 14A may be combined in advance and inserted into the housing 25 when the drug solution injection device 10 is used. In this case, it is preferable that a mounting portion for mounting the plunger mechanism 14A on the barrel 12 is provided in the plunger mechanism 14A and the barrel 12.

Figure 2:
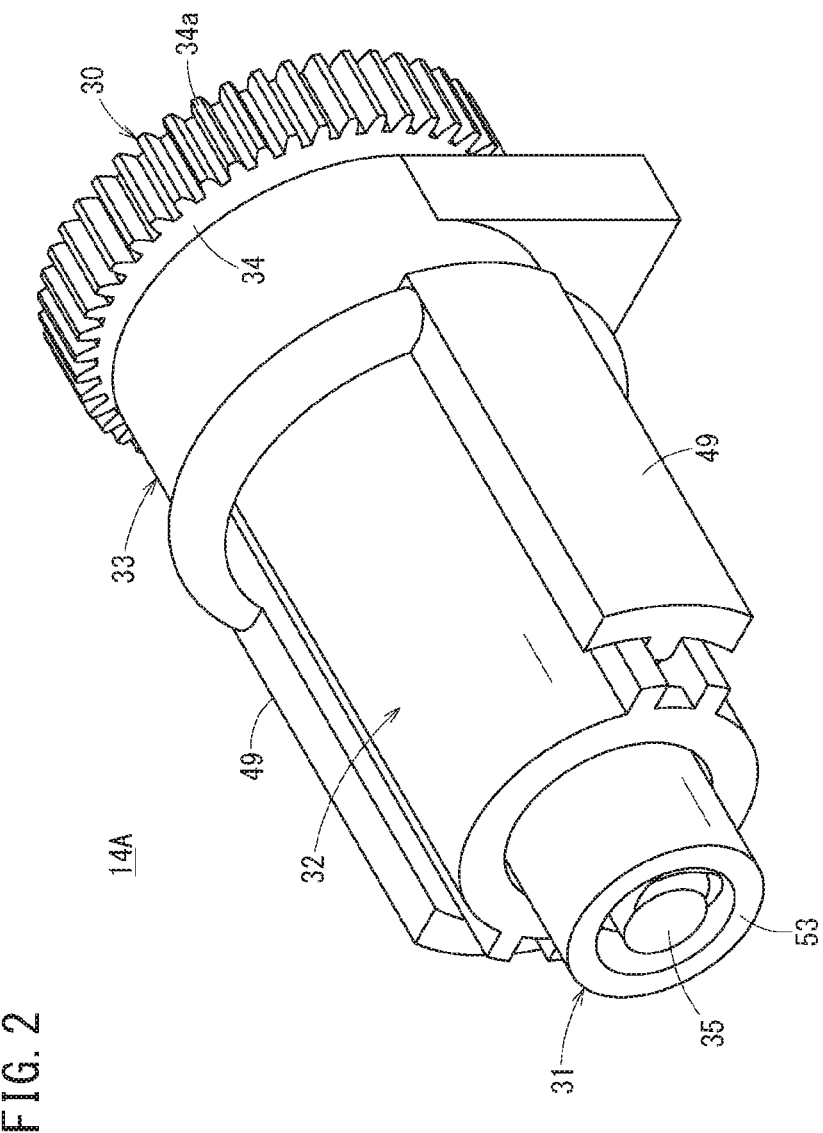
FIG. 2 is a perspective view of an initial state of a plunger mechanism according to a first configuration example.
Figure 3:
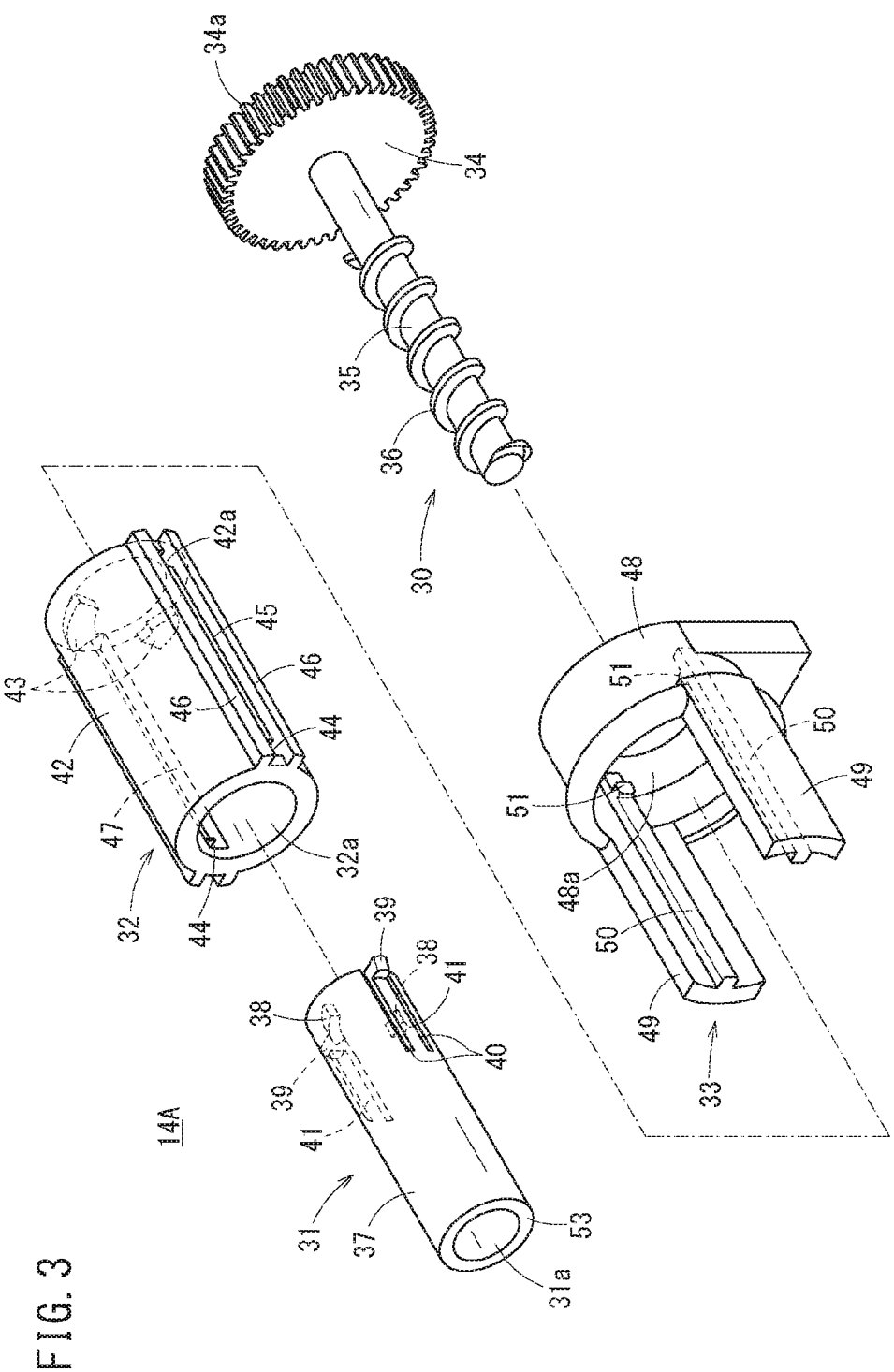
FIG. 3 is an exploded perspective view of the plunger mechanism illustrated in FIG. 2.

Next, the configuration of the plunger mechanism 14A will be described in detail. As illustrated in FIGS. 2 and 3, the plunger mechanism 14A is provided with the rotatable rotation member 30, a first moving member 31 movable in the axial direction with respect to the rotation member 30, a second moving member 32 movable in the axial direction with respect to the rotation member 30, and a support member 33 supporting the second moving member 32 movably in the axial direction.

As illustrated in FIG. 3, the rotation member 30 has a gear portion 34 having a tooth portion 34a formed in the outer peripheral portion thereof, a shaft portion 35 protruding in the tip direction from the center portion of the gear portion 34, and a screw portion 36 formed in a spiral shape on the outer peripheral surface of the shaft portion 35. The tooth portion 34a of the gear portion 34 meshes with the output gear 29a (see FIG. 1) of the drive unit 23 described above. The rotation member 30 is rotationally driven by rotation of the output gear 29a. The rotation member 30 is disposed such that the rotation axis of the gear portion 34 is positioned on a central axis a (see FIG. 1) of the barrel 12. Further, the rotation member 30 is restricted so as not to move relative to the barrel 12 in the axial direction.

The shaft portion 35 extends along the rotation axis of the gear portion 34 on the rotation axis. In the initial state of the plunger mechanism 14A, at least the tip side of the shaft portion 35 is inserted in the barrel 12 (see FIG. 1). The screw portion 36 has the form of a male screw protruding radially outward from the outer peripheral surface of the shaft portion 35. The screw portion 36 is formed from the proximal end side of the shaft portion 35 (position slightly closer to the tip side than the proximal end of the shaft portion 35) to the tip of the shaft portion 35.

The first moving member 31 is formed of a hollow tubular body having a first lumen 31a and is disposed outside the shaft portion 35 of the rotation member 30. The above-described gasket 22 (see FIG. 1) is disposed in front of the first moving member 31. The first moving member 31 is capable of advancing with respect to the rotation member 30, the second moving member 32, and the support member 33. Specifically, the first moving member 31 has a first tubular body portion 37 formed in a hollow cylindrical shape, a first projection portion 38 engageable with the screw portion 36 of the rotation member 30, a claw portion 39 (first engagement portion) engageable with an engagement groove portion 44 (described later) of the second moving member 32, and a pressing portion 53 capable of pressing the gasket 22. The tip surface of the first moving member 31 constitutes the pressing portion 53. The first tubular body portion 37 has a tip opening and a proximal end opening. The first lumen 31a is formed between the tip opening and the proximal end opening.

The first projection portion 38 protrudes radially inward from the inner peripheral surface of the proximal end portion of the first tubular body portion 37. A plurality of (two in the illustrated example) the first projection portions 38 is provided at intervals in the circumferential direction. The plurality of first projection portions 38 is provided at intervals in the circumferential direction and provided at different positions in the axial direction of the first moving member 31 so as to be disposed on a spiral having the same shape as the spiral shape of the screw portion 36. It should be noted that only one first projection portion 38 may be provided as well.

The claw portion 39 is elastically supported. Specifically, the claw portion 39 protrudes outward from the proximal end of an elastic piece 41 elastically deformable in the inward-outward direction (radial direction) of the first moving member 31. The elastic piece 41 is provided on the proximal end side of the first tubular body portion 37. Two parallel slits 40 open in the proximal end direction and penetrating the first tubular body portion 37 in the thickness direction of the first tubular body portion 37 are formed in the first tubular body portion 37. The elastic piece 41 is formed between the two slits 40.

In the first moving member 31, a plurality of (two in the illustrated example) the elastic pieces 41 is provided at intervals in the circumferential direction. The elastic piece 41 is provided at a circumferential position different from the first projection portion 38 described above. Incidentally, although only one elastic piece 41 having the claw portion 39 may be provided as well, it is preferable that the plurality of elastic pieces 41 is provided at equal intervals in the circumferential direction. The claw portion 39 is inserted in a guide groove 47 (described later) of the second moving member 32. As a result, the first moving member 31 can be displaced in the axial direction with respect to the second moving member 32 with rotation about the axis with respect to the second moving member 32 restricted.

The second moving member 32 is formed of a hollow tubular body having a second lumen 32a and is disposed outside the first moving member 31. The second moving member 32 is capable of advancing with respect to the rotation member 30 and the support member 33. The second moving member 32 has a second tubular body portion 42 formed in a hollow cylindrical shape, a second projection portion 43 engageable with the screw portion 36 of the rotation member 30, and the engagement groove portion 44 (second engagement portion) engageable with the claw portion 39 (first engagement portion) of the first moving member 31. The second tubular body portion 42 has a tip opening and a proximal end opening. The second lumen 32a is formed between the tip opening and the proximal end opening.

A recessed guide rail 45 (guide portion) extending along the axial direction is provided in the outer peripheral portion of the second tubular body portion 42. Specifically, two ridges 46 extending in parallel to each other and close to each other in the circumferential direction are formed on the outer peripheral portion of the second tubular body portion 42, and the guide rail 45 is formed between the two ridges 46. In the second tubular body portion 42, two guide rails 45 are provided at intervals in the circumferential direction. Incidentally, although only one guide rail 45 may be provided as well, it is preferable that a plurality of the guide rails 45 is provided at equal intervals in the circumferential direction.

A hole portion 42a is provided in the proximal end portion of the second tubular body portion 42. The hole portion 42a constitutes a temporary fixing mechanism that releasably restricts (temporarily fixes) the second moving member 32 together with a protruding portion 51 (described later) of the support member 33 so as not to advance with respect to the support member 33. Specifically, the hole portion 42a is provided in the bottom portion of the recessed guide rail 45 and penetrates the peripheral wall portion of the second tubular body portion 42 in the thickness direction. A recessed portion open to the bottom portion of the guide rail 45 may be provided in place of the hole portion 42a as well.

The second projection portion 43 protrudes radially inward from the inner peripheral surface of the proximal end portion of the second tubular body portion 42. A plurality of (two in the illustrated example) the second projection portions 43 is provided. The plurality of second projection portions 43 is provided at intervals in the circumferential direction and provided at different positions in the axial direction of the second moving member 32 so as to be disposed on a spiral having the same shape as the spiral shape of the screw portion 36. It should be noted that only one second projection portion 43 may be provided as well.

The engagement groove portion 44 is provided in the vicinity of the tip of the second tubular body portion 42. The guide groove 47 extending in the axial direction is provided in the inner peripheral surface of the second tubular body portion 42, and the engagement groove portion 44 is provided in the tip portion of the guide groove 47. The engagement groove portion 44 in the illustrated example is a through hole penetrating the peripheral wall portion of the second tubular body portion 42 in the thickness direction. The engagement groove portion 44 may be a bottomed hole (recessed portion) open to the second lumen 32a and having a depth toward the radially outer side of the second tubular body portion 42. In the second moving member 32, a plurality of (two in the illustrated example) the engagement groove portions 44 is provided at intervals in the circumferential direction. Incidentally, although only one engagement groove portion 44 may be provided as well, it is preferable that the plurality of engagement groove portions 44 is provided at equal intervals in the circumferential direction so as to correspond to the claw portions 39 of the first moving member 31. In the second moving member 32, a plurality of (two in the illustrated example) the guide grooves 47 is provided at intervals in the circumferential direction. Incidentally, although only one guide groove 47 may be provided as well, it is preferable that the plurality of guide grooves 47 is provided at equal intervals in the circumferential direction so as to correspond to the claw portions 39 of the first moving member 31.

The support member 33 has a base portion 48 fixed to the inner surface of the housing 25 and a plurality of (two in the illustrated example) support arms 49 extending from the base portion 48 in the tip direction. The base portion 48 has a through hole 48a. The shaft portion 35 of the rotation member 30 is inserted in the through hole 48a. The support arms 49 extend in parallel to each other. A guide projection 50 protruding inward is provided inside each support arm 49. The guide projection 50 extends in parallel to the axial direction of the second moving member 32. The guide projection 50 is inserted in the guide rail 45 of the second moving member 32. As a result, the second moving member 32 can be displaced in the axial direction with respect to the rotation member 30 and the support member 33 with rotation about the axis restricted. Incidentally, although only one support arm 49 may be provided as well, it is preferable that the plurality of support arms 49 is provided at equal intervals in the circumferential direction so as to correspond to the guide rails 45 of the second moving member 32. Inclination of the second moving member 32 with respect to the support member 33 is suppressed because the plurality of (two in the illustrated example) guide rails 45 and the plurality of (two in the illustrated example) support arms 49 having the guide projections 50 are provided at equal intervals in the circumferential direction in this manner.

The protruding portion 51 protruding inward is provided in the proximal end portion of the guide projection 50. In the initial state of the plunger mechanism 14A, the protruding portion 51 is inserted in the hole portion 42a (the protruding portion 51 and the hole portion 42a are engaged). As a result, the second moving member 32 is temporarily fixed with respect to the support member 33. Once a predetermined or larger force in the tip direction is applied to the second moving member 32, the engagement between the protruding portion 51 and the hole portion 42a is released and the second moving member 32 advances by means of the force in the tip direction.

Next, the action and effect of the drug solution injection device 10 provided with the plunger mechanism 14A configured as described above will be described.

When the drug solution injection device 10 illustrated in FIG. 1 is used, the injection line 16 (such as the needle-attached tube 17 described above) is connected to the drug solution injection device 10. Then, the drug solution injection device 10 is attached to a patient by adhering onto the skin S, mounting onto clothes, or the like. Next, the needle 21 punctures the skin S. Incidentally, the drug solution injection device 10 may be attached to the patient before the needle 21 punctures the skin S as well.

Then, once the drug solution injection device 10 receives a predetermined operation initiation command, the plunger mechanism 14A extends in a plurality of stages under the drive action of the drive unit 23. In conjunction with this extension operation, the gasket 22 is pressed against the plunger mechanism 14A and advances. As a result, the drug solution M in the barrel 12 is pushed out. The drug solution M pushed out from the inside of the barrel 12 is injected (injected) into the body of the patient via the injection line 16 puncturing the patient. Specifically, the extension operation of the plunger mechanism 14A has a first extension operation and a second extension operation subsequent to the first extension operation as described below.

Figure 4:
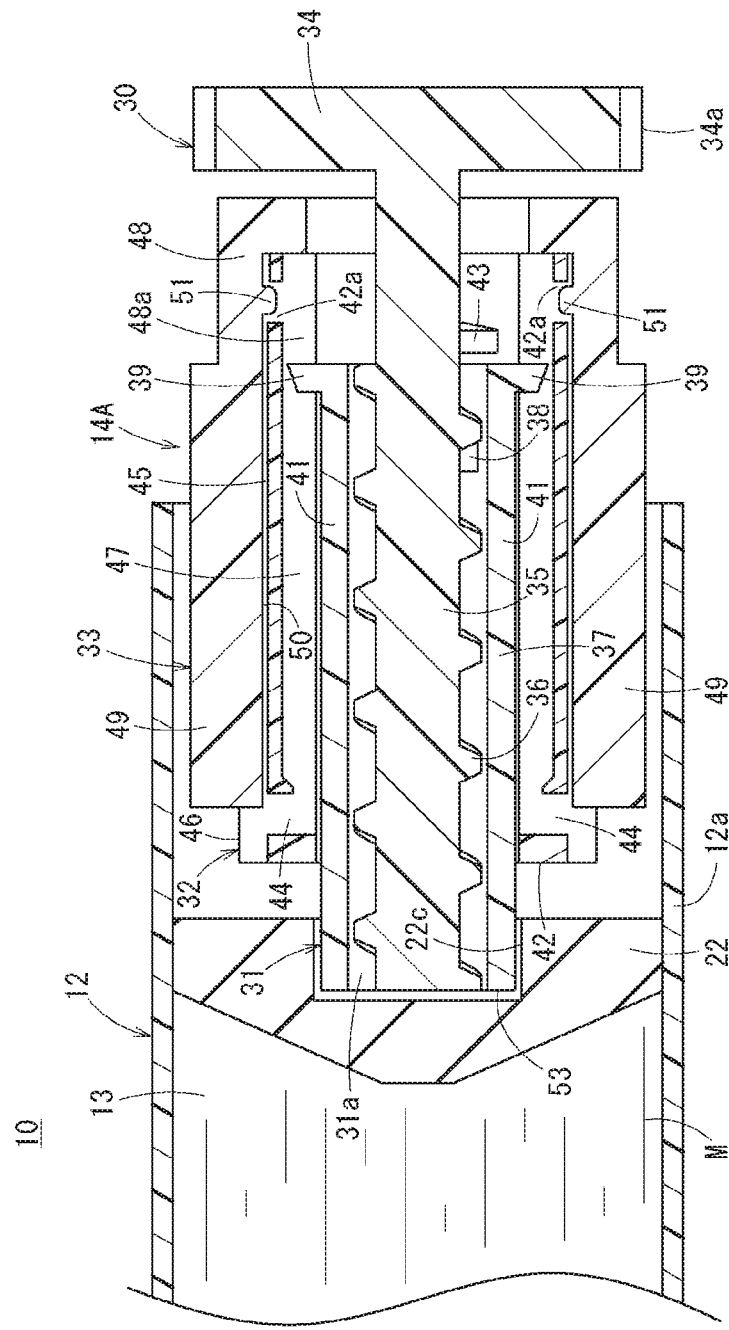
FIG. 4 is a cross-sectional view of the initial state of the plunger mechanism illustrated in FIG. 2.

As illustrated in FIG. 4, in the initial state of the plunger mechanism 14A (state in which the plunger mechanism 14A is yet to be operated and the drug solution M is yet to be discharged from the inside of the barrel 12), each portion of the plunger mechanism 14A is as follows. The rotation member 30, the first moving member 31, and the second moving member 32 are disposed at positions overlapping each other in the axial direction. The screw portion 36 of the rotation member 30 and the first projection portion 38 of the first moving member 31 are engaged. The screw portion 36 of the rotation member 30 and the second projection portion 43 of the second moving member 32 are not engaged. The claw portion 39 (first engagement portion) and the engagement groove portion 44 (second engagement portion) are not engaged. The hole portion 42a of the second moving member 32 and the protruding portion 51 of the support member 33 are engaged. The pressing portion 53, which is the tip surface of the first moving member 31, is inserted in a groove 22c provided in the proximal end surface of the gasket 22. The pressing portion 53 is away from the bottom portion of the groove 22c. The inner diameter of the groove 22c is slightly larger than the outer diameter of the tip portion of the first moving member 31. Incidentally, in the initial state, the pressing portion 53 may abut against the bottom portion of the groove 22c. The groove 22c may not be provided in the proximal end surface of the gasket 22.

Figure 5:
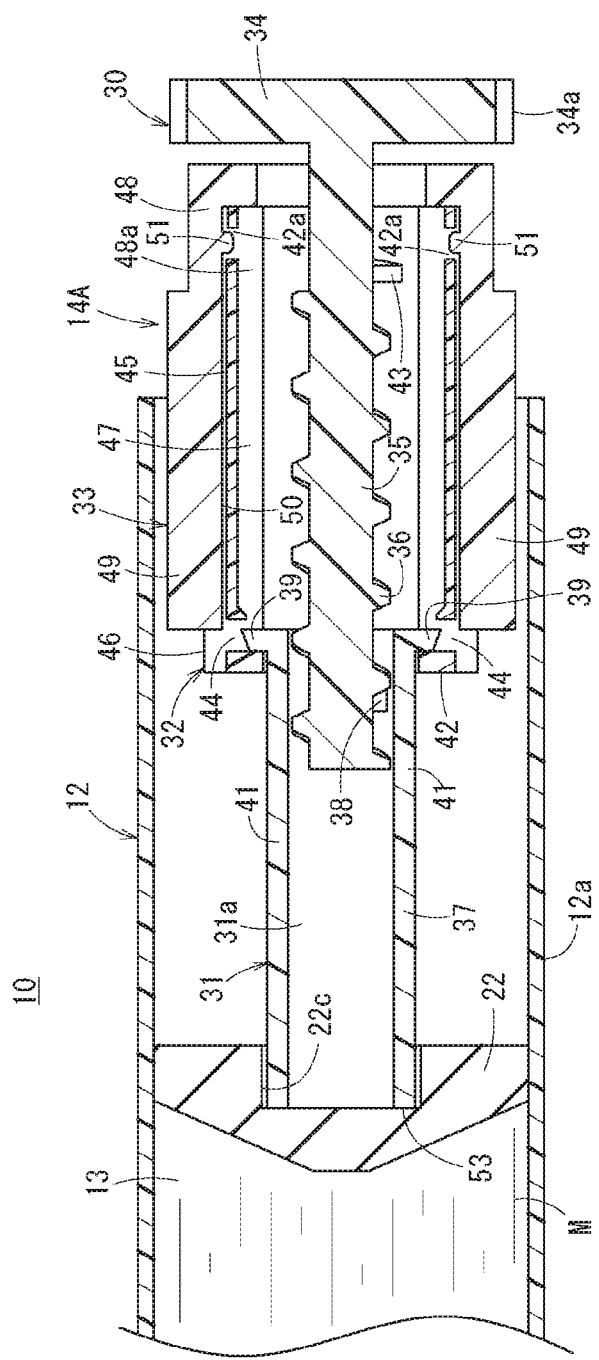
FIG. 5 is a cross-sectional view of a state in which a first moving member has advanced with respect to a second moving member in the plunger mechanism illustrated in FIG. 2.

In the first extension operation of the plunger mechanism 14A, the rotation member 30 rotates from the initial state. As illustrated in FIG. 5, in conjunction with this rotation and under the engagement action of the screw portion 36 and the first projection portion 38, the first moving member 31 advances to a predetermined position with respect to the rotation member 30 and the second moving member 32. In this case, rotation of the first moving member 31 about the axis relative to the second moving member 32 is restricted and rotation of the second moving member 32 about the axis relative to the support member 33 is restricted, and thus the first moving member 31 does not rotate along with the rotation of the rotation member 30. In other words, the first projection portion 38 does not rotate. Accordingly, the first projection portion 38 is sent in the tip direction by the rotating screw portion 36. As a result, the first moving member 31 advances.

With the first moving member 31 moving from the position of FIG. 4 to the position of FIG. 5, the pressing portion 53 of the first moving member 31 abuts against the bottom portion of the groove 22c of the gasket 22. Then, after this abutting, the gasket 22 is pressed in the tip direction by the pressing portion 53 as the first moving member 31 advances, and the gasket 22 advances together with the first moving member 31 in the barrel 12. As the gasket 22 advances, the drug solution M is discharged via the discharge port 12e (see FIG. 1) of the barrel 12. When the gasket 22 advances, the tip portion of the first moving member 31 is inserted into the groove 22c of the gasket 22, and thus the first moving member 31 is prevented from being inclined in the barrel 12. As a result, the pressing portion 53 of the first moving member 31 is prevented from pressing the gasket 22 in a direction inclined with respect to the axis of the barrel 12.

Further, as illustrated in FIG. 5, the claw portion 39 and the engagement groove portion 44 are engaged when the first moving member 31 has advanced to the predetermined position with respect to the second moving member 32 by the rotation of the rotation member 30. As a result, a state occurs where axial displacement of the first moving member 31 relative to the second moving member 32 is restricted. In addition, inclination of the first moving member 31 with respect to the second moving member 32 is suppressed because the plurality of (two in the illustrated example) claw portions 39 and the plurality of (two in the illustrated example) engagement groove portions 44 are provided at equal intervals in the circumferential direction.

During the first extension operation, the second moving member 32 receives a force in the tip direction from the first moving member 31 due to the frictional resistance between the first moving member 31 and the second moving member 32. However, the hole portion 42a of the second moving member 32 and the protruding portion 51 of the support member 33 are engaged. The engagement force of the hole portion 42a and the protruding portion 51 is larger than the force in the tip direction that the second moving member 32 receives from the first moving member 31 by the frictional resistance. Accordingly, the second moving member 32 does not advance during the first extension operation.

Figure 6:
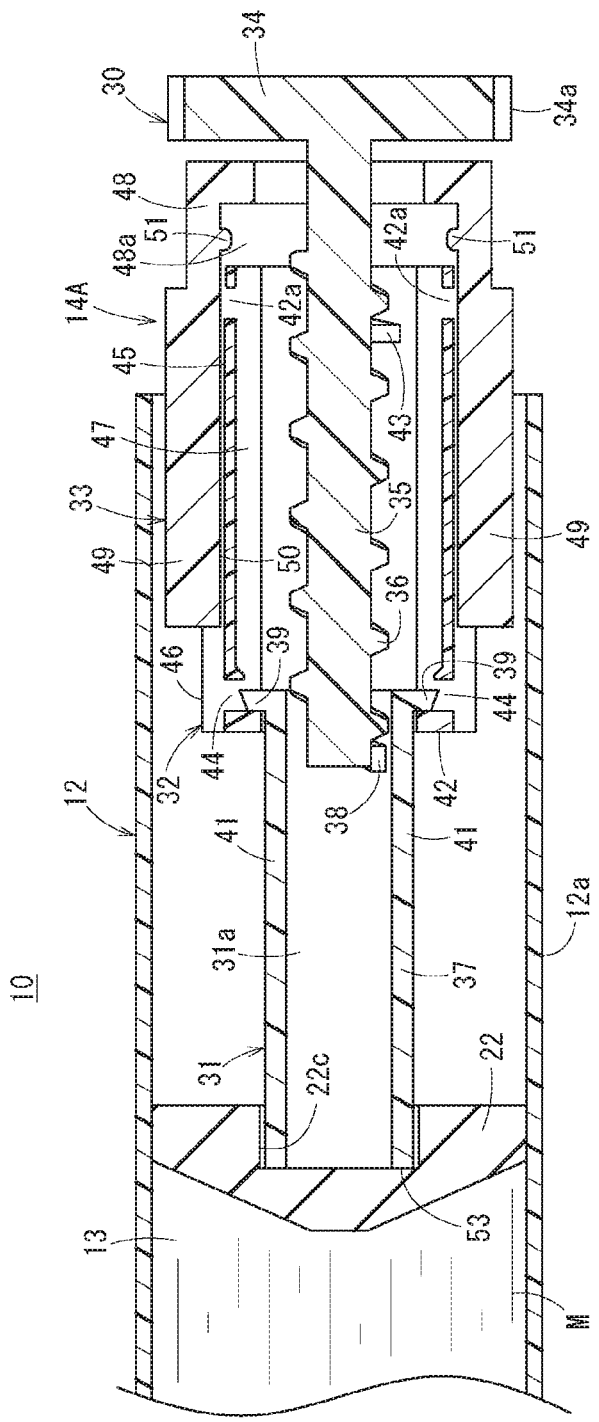
FIG. 6 is a cross-sectional view of a state in which the second moving member has slightly further advanced from the state illustrated in FIG. 5.

In the state that is illustrated in FIG. 5, the engagement between the screw portion 36 and the first projection portion 38 is maintained. Accordingly, once the rotation member 30 further rotates from the state illustrated in FIG. 5, the first moving member 31 further advances under the engagement action of the screw portion 36 and the first projection portion 38 as illustrated in FIG. 6. At this time, the claw portion 39 and the engagement groove portion 44 are engaged, and thus the second moving member 32 advances together with the first moving member 31 by being pulled in the tip direction by the first moving member 31. The force with which the first moving member 31 pulls the second moving member 32 in the tip direction in a state in which the claw portion 39 and the engagement groove portion 44 are engaged is larger than the engagement force of the hole portion 42a of the second moving member 32 and the protruding portion 51 of the support member 33. Accordingly, the hole portion 42a climbs over the protruding portion 51, and the engagement between the hole portion 42a and the protruding portion 51 is released as a result. The gasket 22 advances in the barrel 12, by being pressed by the pressing portion 53 of the first moving member 31, during the course of a transition from the state of FIG. 5 to the state of FIG. 6 as well.

Figure 7:
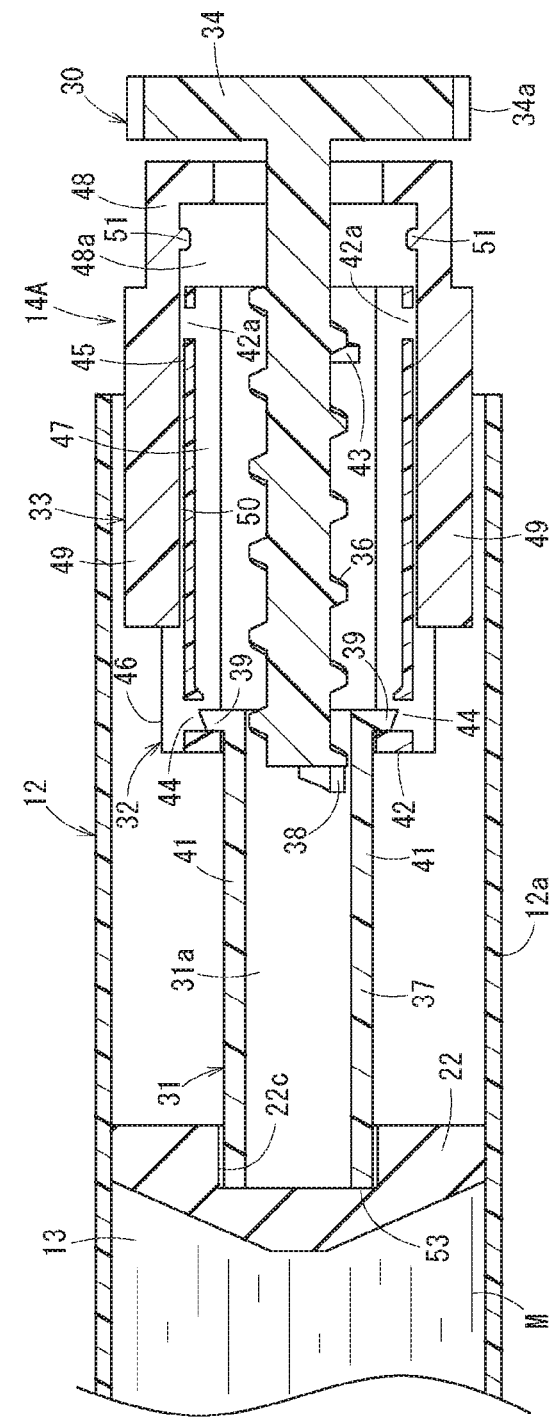
FIG. 7 is a cross-sectional view of a state in which a screw portion and a first projection portion are disengaged and the screw portion and a second projection portion are engaged by the second moving member slightly further advancing from the state illustrated in FIG. 5.

When the first moving member 31 and the second moving member 32 further advance as the rotation member 30 further rotates from the state illustrated in FIG. 6, engagement between the screw portion 36 and the second projection portion 43 is initiated and the screw portion 36 and the first projection portion 38 are disengaged as illustrated in FIG. 7. Specifically, the screw portion 36 and the first projection portion 38 are disengaged after the screw portion 36 and the second projection portion 43 are engaged. The gasket 22 advances in the barrel 12, by being pressed by the pressing portion 53 of the first moving member 31, during the course of a transition from the state of FIG. 6 to the state of FIG. 7 as well.

Figure 8:
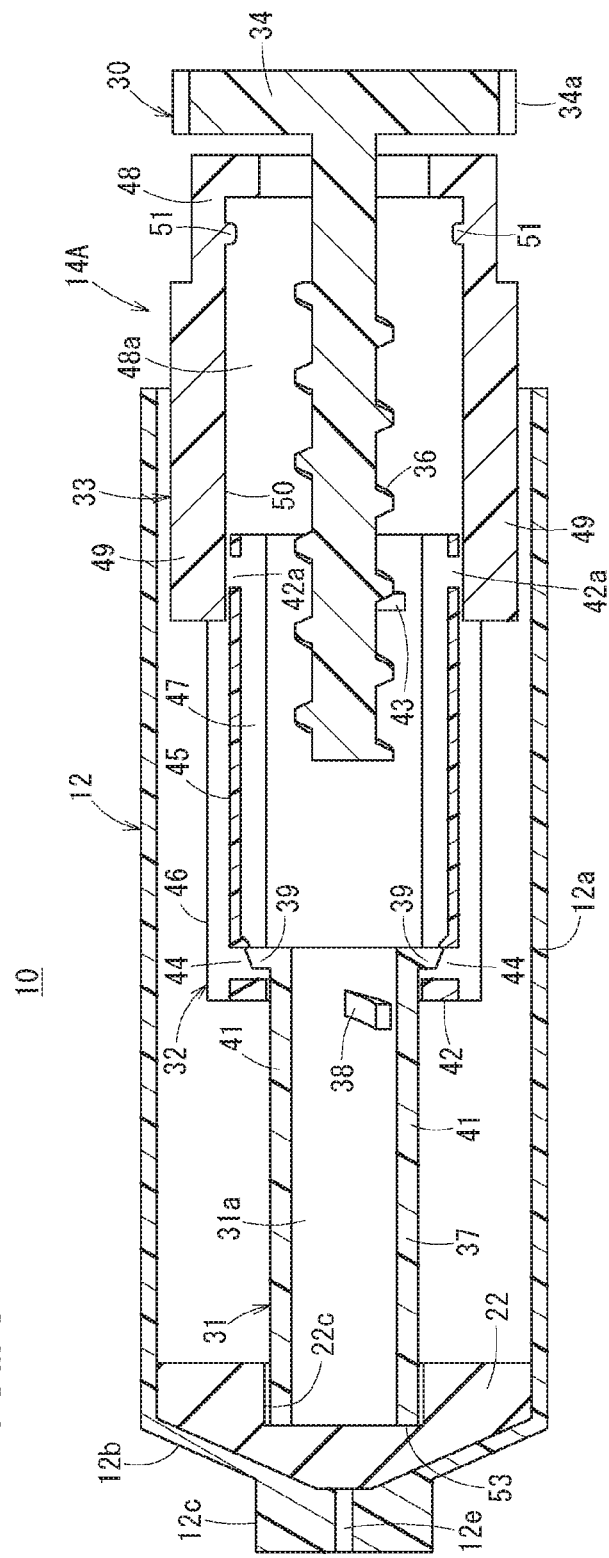
FIG. 8 is a cross-sectional view of a state in which an extension operation of the plunger mechanism illustrated in FIG. 2 is completed.

Next, in the second extension operation of the plunger mechanism 14A, the rotation member 30 further rotates from the state illustrated in FIG. 7. As illustrated in FIG. 8, in conjunction with this rotation and under the engagement action of the screw portion 36 and the second projection portion 43, the second moving member 32 advances with respect to the rotation member 30 together with the first moving member 31. At this time, the engagement between the screw portion 36 and the first projection portion 38 is released, and thus the first moving member 31 is not directly driven by the rotation member 30. However, the claw portion 39 and the engagement groove portion 44 are engaged, and thus the first moving member 31 is pressed in the tip direction by the second moving member 32 to advance together with the second moving member 32. The gasket 22 advances in the barrel 12, by being pressed by the pressing portion 53 of the first moving member 31, during the course of a transition from the state of FIG. 7 to the state of FIG. 8 as well. Subsequently, the first moving member 31 and the second moving member 32 stop advancing when the gasket 22 reaches the most distal position in the movable range (when the gasket 22 abuts against the shoulder portion 12b of the barrel 12). In other words, the extension of the plunger mechanism 14A is completed.

As described above, in the drug solution injection device 10 according to the present embodiment, the plunger mechanism 14A extends over a plurality of stages, and thus it is possible to shorten the plunger mechanism 14A and the drug solution injection device 10 can be reduced in size to the same extent. The area that is required for adhering in the case of adhering to the surface of a patient's body can be reduced from the device size reduction, and thus, embodiments of the present disclosure can be easily applied to applications such as adhering to the surface of a patient's body as well. Further, the device size reduction can lead to usability improvement in terms of portability, storage, and so on.

Incidentally, in a case where the gasket 22 is pushed with a spring, air, or the like, it is difficult to control the speed at which the drug solution M is injected in a constant manner. Meanwhile, with the drug solution injection device 10 according to certain embodiments described herein, the drug solution M can be injected at a constant speed because an engagement structure (engagement between the screw portion 36 and the first projection portion 38 and engagement between the screw portion 36 and the second projection portion 43) mechanically moves a movable portion (first moving member 31 and second moving member 32).

According to the drug solution injection device 10, the claw portion 39 and the engagement groove portion 44 are engaged when the first moving member 31 has advanced to a predetermined position with respect to the second moving member 32. Then, axial displacement of the first moving member 31 relative to the second moving member 32 is restricted. With this configuration, the second moving member 32 is capable of causing the first moving member 31 to advance in a reliable manner when the second moving member 32 advances with respect to the rotation member 30.

During the second extension operation in the drug solution injection device 10, the screw portion 36 and the second projection portion 43 are engaged in conjunction with rotation of the rotation member 30, and then the screw portion 36 and the first projection portion 38 are disengaged. With this configuration, the engagement opponent of the screw portion 36 can be timely changed from the first projection portion 38 to the second projection portion 43, and thus a transition from the first extension operation to the second extension operation can be smoothly performed.

The drug solution injection device 10 is provided with the elastically supported claw portion 39 and the engagement groove portion 44 with which the claw portion 39 is engageable. Accordingly, the claw portion 39 and the engagement groove portion 44 can be quickly engaged at a point in time when the first moving member 31 has advanced to the maximum with respect to the second moving member 32, and thus the first moving member 31 can be swiftly locked with respect to the second moving member 32 through a linear movement alone.

In the drug solution injection device 10, the screw portion 36 has the form of a male screw, the first moving member 31 is formed of a hollow tubular body having the first lumen 31a, the first projection portion 38 protrudes toward the inside of the first moving member 31, and the male screw is inserted in the first lumen 31a in the initial state. Furthermore, the second moving member 32 is formed of a hollow tubular body having the second lumen 32a, the second projection portion 43 protrudes toward the inside of the second moving member 32, and the male screw and the first moving member 31 are inserted in the second lumen 32a. With this configuration, the outer diameter size of the plunger mechanism 14A can be reduced with ease.

The drug solution injection device 10 is provided with the support member 33 that guides the second moving member 32 in the axial direction while restricting rotation of the second moving member 32. The second moving member 32 has the guide groove 47 (guide portion) that guides the first moving member 31 in the axial direction while restricting rotation of the first moving member 31. With this configuration, it is possible to prevent the first moving member 31 and the second moving member 32 from rotating along with rotation of the rotation member 30, and thus the rotation operation of the rotation member 30 can be appropriately converted into the axial operations of the first moving member 31 and the second moving member 32. In addition, because the plurality of (two in the illustrated example) claw portions 39 and the plurality of (two in the illustrated example) guide grooves 47 are provided at equal intervals in the circumferential direction, inclination of the first moving member 31 with respect to the second moving member 32 is suppressed.

In the drug solution injection device 10, the support member 33 and the second moving member 32 (protruding portion 51 and hole portion 42a) are engaged such that the position of the second moving member 32 with respect to the rotation member 30 is maintained until termination of the first extension operation. Engagement between the support member 33 and the second moving member 32 is released by the rotation member 30 rotating in a state in which the screw portion 36 and the first projection portion 38 are engaged.

With this configuration, it is possible to prevent the second moving member 32 from advancing by being pulled by the advancing of the first moving member 31 during the first extension operation.

In the drug solution injection device 10, the plunger mechanism 14A described above (hereinafter, also referred to as the "plunger mechanism 14A according to the first configuration example") may be replaced with, for example, plunger mechanisms 14B to 14E according to the following second to fifth configuration examples.

Figure 9:
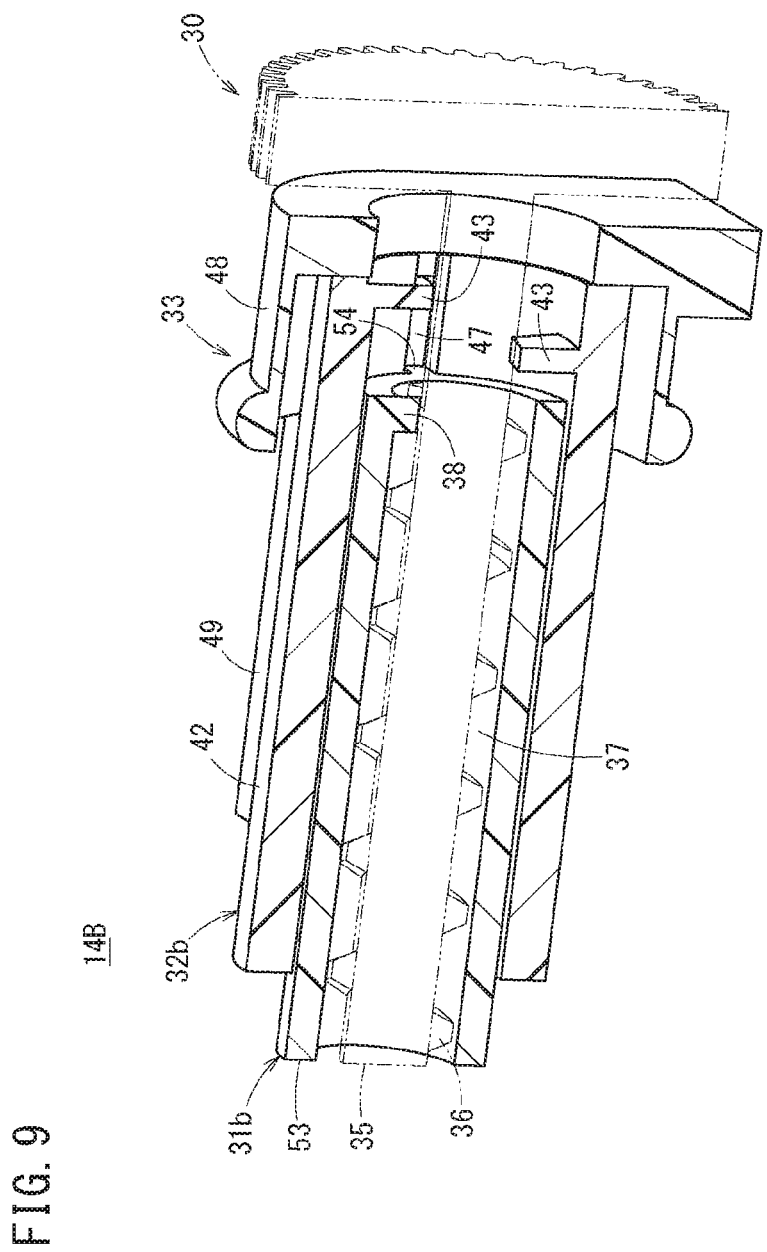
FIG. 9 is a perspective cross-sectional view of an initial state of a plunger mechanism according to a second configuration example.

The plunger mechanism 14B according to the second configuration example illustrated in FIG. 9 differs from the above-described plunger mechanism 14A in terms of the configurations of a first moving member 31b and a second moving member 32b.

Figure 10A:
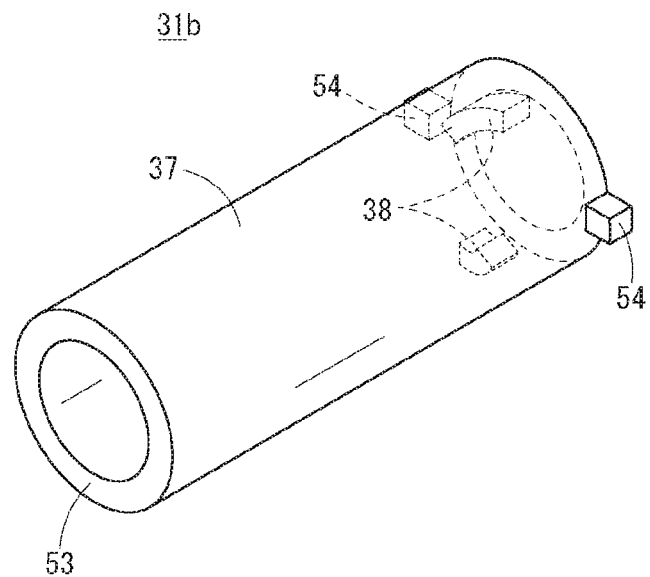
FIG. 10A is a perspective view of a first moving member of the plunger mechanism illustrated in FIG. 9.

As illustrated in FIG. 10A, the first moving member 31b has a projecting portion 54 (first engagement portion) protruding outward from the proximal end portion outer surface of the first tubular body portion 37. The projecting portion 54 is engageable with a lock groove 55 (see FIG. 10B) to be described later. A plurality of (two in the illustrated example) the projecting portions 54 is provided at intervals in the circumferential direction. Although only one projecting portion 54 may be provided as well, it is preferable that the plurality of projecting portions 54 is provided at equal intervals in the circumferential direction. Incidentally, as in the case of the first moving member 31 of the plunger mechanism 14A, the first projection portion 38 (see FIG. 9) is provided in the inner peripheral portion of the first moving member 31b.

Figure 10B:
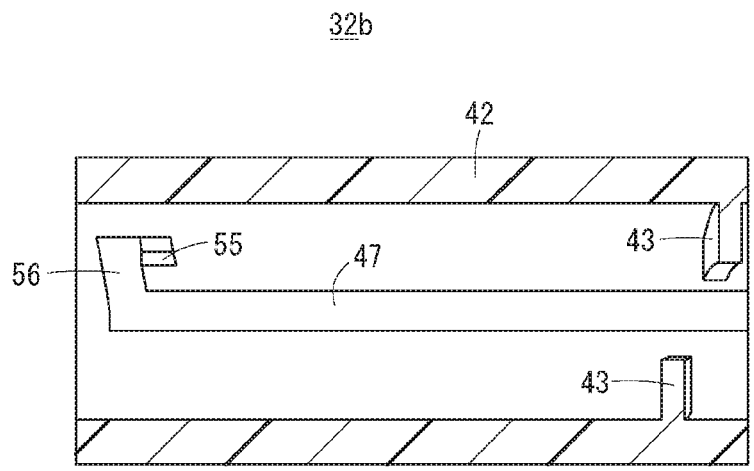
FIG. 10B is a cross-sectional view of a second moving member of the plunger mechanism illustrated in FIG. 9.

As illustrated in FIG. 10B, the inner peripheral portion of the second moving member 32b is provided with the guide groove 47 similar to the guide groove 47 of the second moving member 32, the lock groove 55 (second engagement portion) shorter than the guide groove 47, and a relay groove 56 connecting one end (tip) of the guide groove 47 and one end (tip) of the lock groove 55. The lock groove 55 communicates with the guide groove 47 via the relay groove 56 and extends in the proximal end direction from the relay groove 56. The lock groove 55 extends in parallel to the guide groove 47 and slightly extends in the proximal end direction from the end portion of the relay groove 56 on the side opposite to the guide groove 47. Accordingly, the proximal end of the lock groove 55 is closer to the tip side than the proximal end of the guide groove 47. The extension length of the lock groove 55 from the relay groove 56 may be approximately equal to the length of the projecting portion 54 along the axial direction of the first moving member 31b or may be shorter than the length of the projecting portion 54. The relay groove 56 extends in the circumferential direction of the second moving member 32b.

In the second moving member 32b, two groove structures are line-symmetrically provided with respect to the central axis of the second moving member 32b and the guide groove 47, the relay groove 56, and the lock groove 55 constitute each of the groove structures. In a case where only one projecting portion 54 is provided in the first moving member 31b, only one groove structure may be provided in the second moving member 32b. Still, it is preferable that a plurality of the groove structures of the projecting portion 54 of the first moving member 31b and a plurality of the groove structures of the second moving member 32b are provided at equal intervals in the circumferential direction. As a result, inclination of the first moving member 31b with respect to the second moving member 32b is suppressed.

Incidentally, the other parts of the plunger mechanism 14B are similar in configuration to plunger mechanism 14A described above.

As illustrated in FIG. 9, in the initial state of the plunger mechanism 14B, the projecting portion 54 is inserted in the guide groove 47. Once the rotation member 30 rotates from the state illustrated in FIG. 9, the first moving member 31b advances under the engagement action of the screw portion 36 and the first projection portion 38, and the plunger mechanism 14B extends as a result (first extension operation). At this time, the projecting portion 54 advances in the guide groove 47. As the first moving member 31b advances, the projecting portion 54 reaches the most distal portion of the guide groove 47. Then, the projecting portion 54 enters the lock groove 55 via the relay groove 56. As a result, a movement of the first moving member 31b in the proximal end direction relative to the second moving member 32b is restricted (locked).

Specifically, the lock operation restricting a movement of the first moving member 31b in the proximal end direction relative to the second moving member 32b in the plunger mechanism 14B has a rotation operation (FIG. 11) as a first lock operation and a locking operation (FIG. 12) as a second lock operation subsequent to the rotation operation.

Figure 11:
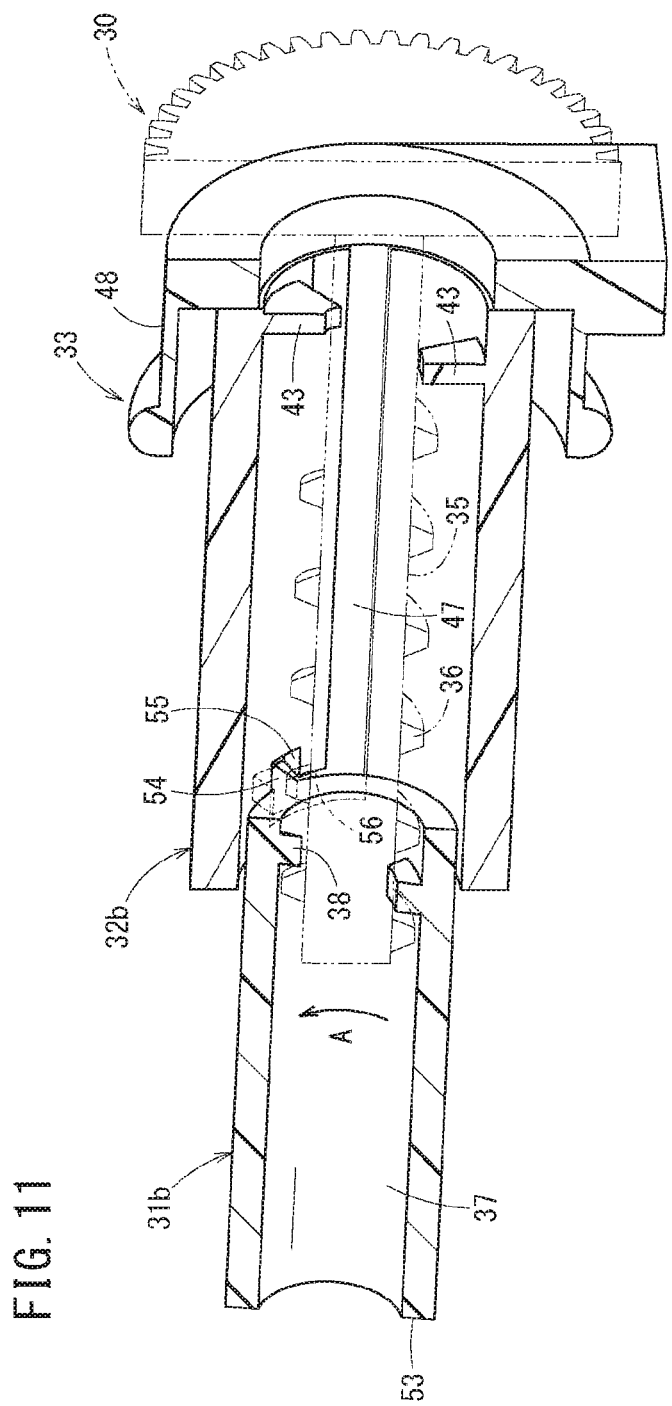
FIG. 11 is a perspective cross-sectional view illustrating a rotation operation of a lock operation of the plunger mechanism illustrated in FIG. 9.

In the rotation operation, the first moving member 31b rotates in the arrow A direction with respect to the second moving member 32b as illustrated in FIG. 11 after the projecting portion 54 reaches the most distal portion of the guide groove 47 as described above. As a result, the projecting portion 54 relatively moves in the relay groove 56 toward the lock groove 55. In other words, the projecting portion 54 moves in the circumferential direction in the relay groove 56. When the projecting portion 54 reaches the most distal portion of the guide groove 47 (end portion of the relay groove 56 on the guide groove 47 side), restriction on rotation of the first moving member 31b relative to the second moving member 32b is released. Accordingly, rotation of the first moving member 31b in the arrow A direction is performed as described above by the rotational force that the first moving member 31b receives from the rotating rotation member 30. As a result, the projecting portion 54 reaches the end portion of the relay groove 56 on the lock groove 55 side.

Figure 12:
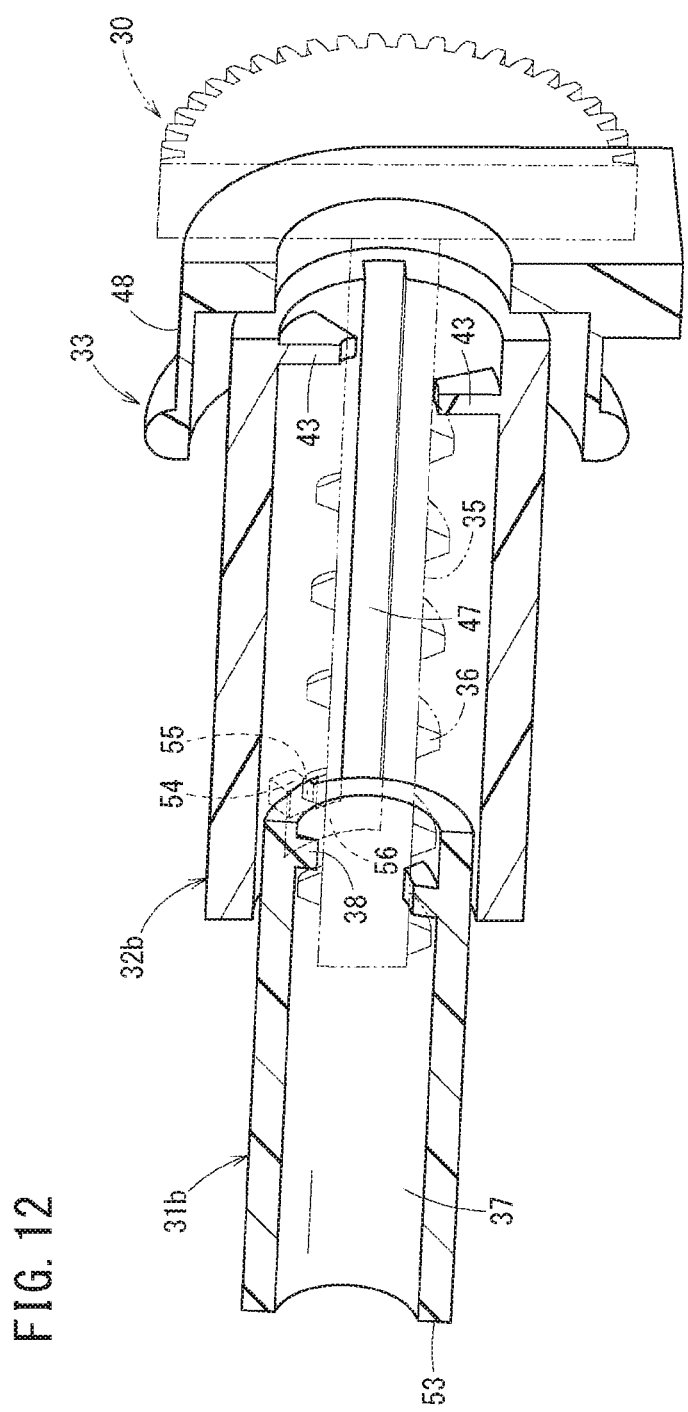
FIG. 12 is a perspective cross-sectional view illustrating a locking operation of the lock operation of the plunger mechanism illustrated in FIG. 9.

Next, in the locking operation, the projecting portion 54 enters the lock groove 55 and the projecting portion 54 is locked in the lock groove 55 by the second moving member 32b advancing with respect to the first moving member 31b as illustrated in FIG. 12. This locking operation is performed after the screw portion 36 of the rotation member 30 and the second projection portion 43 of the second moving member 32b are engaged and the screw portion 36 and the first projection portion 38 of the first moving member 31b are disengaged. Once the rotation member 30 rotates in a state in which the screw portion 36 and the first projection portion 38 of the first moving member 31b are disengaged and the projecting portion 54 is positioned in the end portion of the relay groove 56 on the lock groove 55 side, the second moving member 32b advances under the engagement action of the screw portion 36 and the second projection portion 43.

In the initial stage of the advancing of the second moving member 32b, only the second moving member 32b advances with the first moving member 31b stopped. In other words, the projecting portion 54 enters the lock groove 55 by the first moving member 31b relatively retreating with respect to the second moving member 32b. Then, the projecting portion 54 is locked by the lock groove 55 by the projecting portion 54 abutting against the proximal end side wall of the lock groove 55. In a state in which the projecting portion 54 is locked by the lock groove 55, a movement of the first moving member 31*b* in the proximal end direction relative to the second moving member 32*b* is blocked. Accordingly, after the locking operation is completed, the first moving member 31*b* advances together with the second moving member 32*b* as the rotation member 30 rotates. By the second moving member 32*b* advancing together with the first moving member 31*b* in this manner, the plunger mechanism 14B further extends (second extension operation).

Incidentally, although the barrel 12, the gasket 22, and the drug solution M are not illustrated in FIGS. 9, 11, and 12, the drug solution M is discharged from the barrel 12 by the gasket 22 being pressed by the pressing portion 53 and advancing in the barrel 12 as the first moving member 31*b* advances, which is similar to a case where the plunger mechanism 14A is operated.

In the plunger mechanism 14B configured as described above, the projecting portion 54 is provided on the outer surface of the first moving member 31*b* (outer surface of the first tubular body portion 37). Accordingly, the projecting portion 54 is capable of having higher strength than the claw portion 39 provided in the first moving member 31 of the plunger mechanism 14A described above. Accordingly, it is possible to structurally stabilize the mechanism portion that locks the first moving member 31*b* with respect to the second moving member 32*b*.

Incidentally, the plunger mechanism 14B is identical or similar in action and effect to the plunger mechanism 14A when it comes to the parts of the plunger mechanism 14B according to the second configuration example that are the same as those of the plunger mechanism 14A according to the first configuration example.

Figure 13:
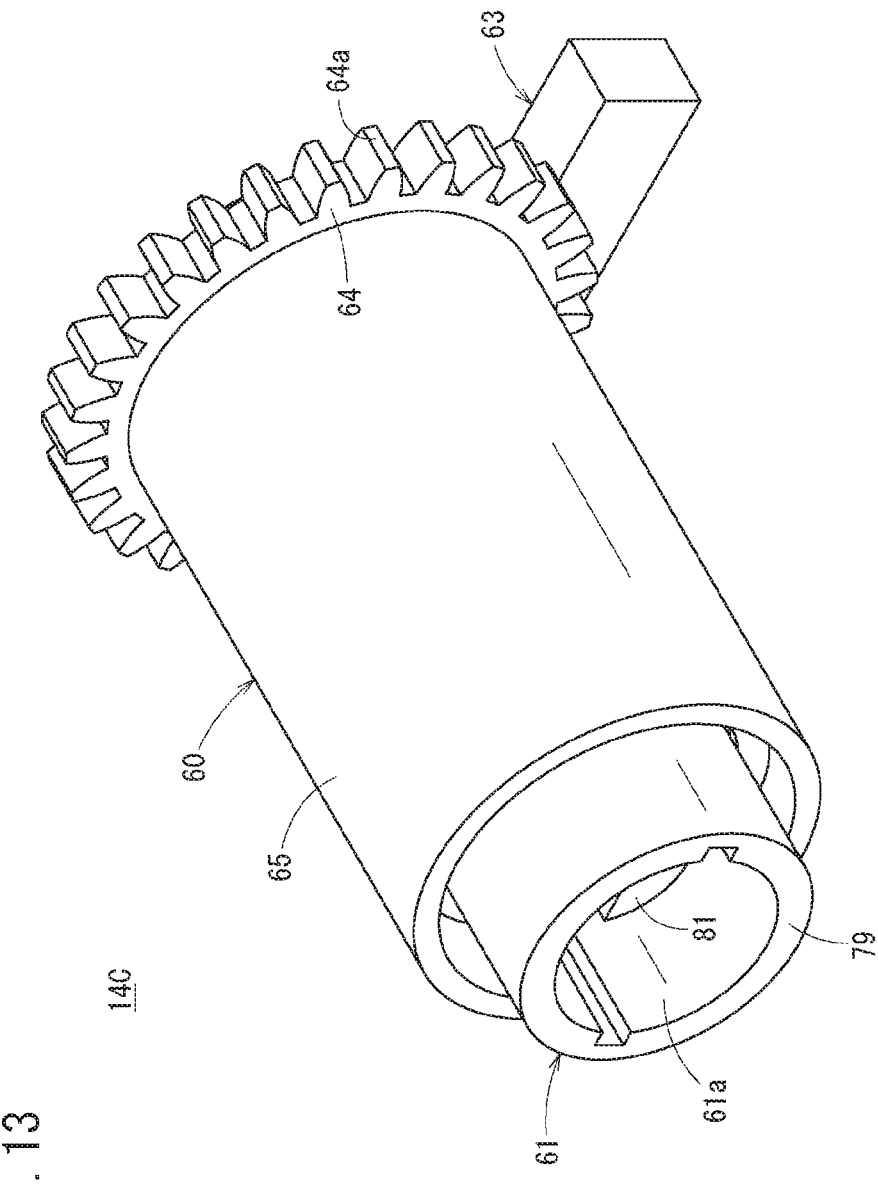
FIG. 13 is a perspective view of an initial state of a plunger mechanism according to a third configuration example.
Figure 14:
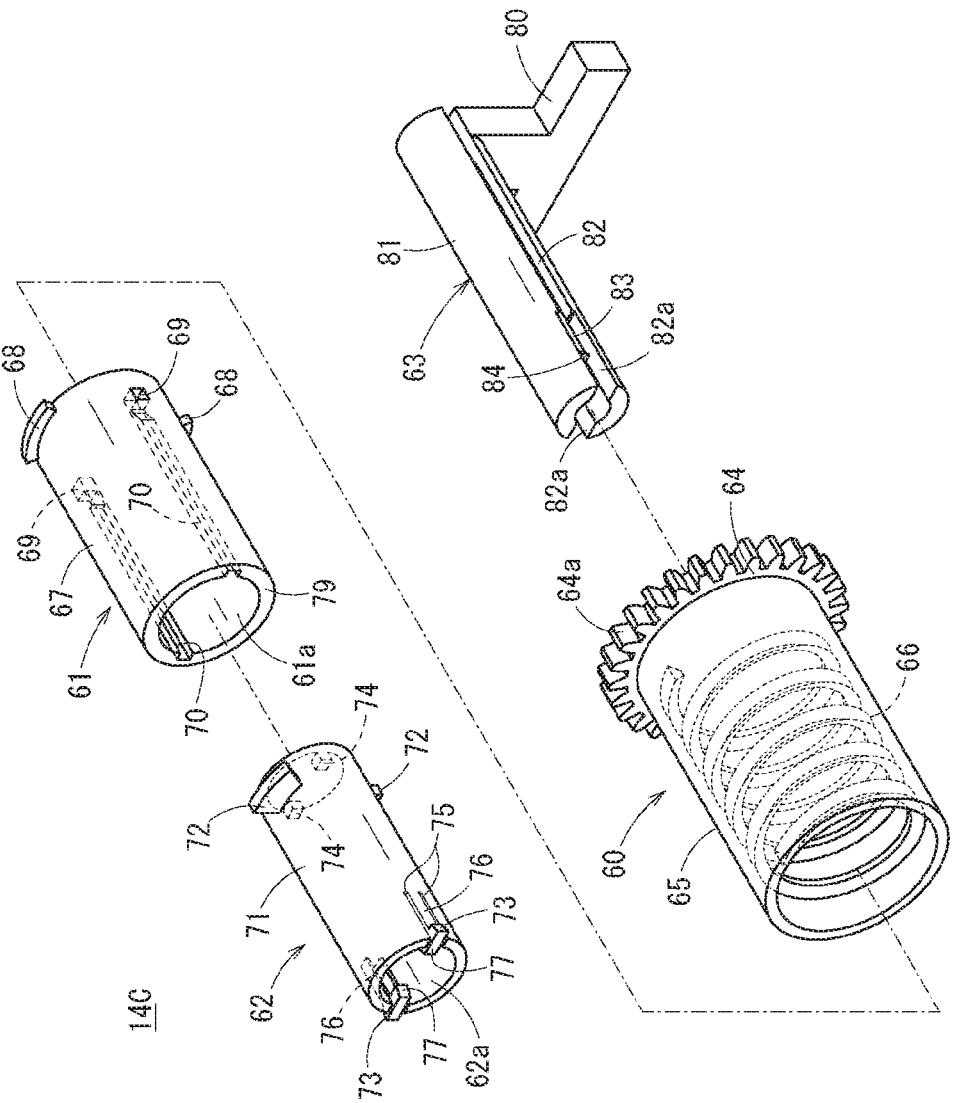
FIG. 14 is an exploded perspective view of the plunger mechanism illustrated in FIG. 13.

The plunger mechanism 14C according to the third configuration example illustrated in FIGS. 13 and 14 is provided with a rotatable rotation member 60, a first moving member 61 movable in the axial direction with respect to the rotation member 60, a second moving member 62 movable in the axial direction with respect to the rotation member 60, and a support member 63 supporting the second moving member 62 movably in the axial direction.

As illustrated in FIG. 14, the rotation member 60 has a gear portion 64 having a tooth portion 64*a* formed in the outer peripheral portion thereof, a tube portion 65 protruding in the tip direction from the gear portion 64 and having a hollow cylindrical shape, and a screw portion 66 formed in a spiral shape on the inner peripheral surface of the tube portion 65. The tooth portion 64*a* of the gear portion 64 meshes with the output gear 29*a* (see FIG. 1) of the power transmission unit 28 described above. The rotation member 60 is rotationally driven by rotation of the output gear 29*a*. The rotation member 60 is disposed such that the rotation axis of the gear portion 64 is positioned on the central axis a (see FIG. 1) of the barrel 12. Further, the rotation member 60 is restricted so as not to move relative to the barrel 12 in the axial direction.

The tube portion 65 extends along the rotation axis of the gear portion 64 on the rotation axis. In the initial state of the plunger mechanism 14C, at least the tip side of the tube portion 65 is inserted in the barrel 12 (see FIG. 1). The screw portion 66 has the form of a female screw protruding radially inward from the inner peripheral surface of the tube portion 65. The screw portion 66 is formed from the tip side to the proximal end side of the tube portion 65.

The first moving member 61 is formed of a hollow tubular body having a first lumen 61*a* and is disposed inside the rotation member 60. The gasket 22 (see FIG. 1) is connected to the tip portion of the first moving member 61. The first moving member 61 is capable of advancing with respect to the rotation member 60, the second moving member 62, and the support member 63. Specifically, the first moving member 61 has a first tubular body portion 67 formed in a hollow cylindrical shape, a first projection portion 68 engageable with the screw portion 66 of the rotation member 60, an engagement groove portion 69 (first engagement portion) engageable with a claw portion 73 (described later) of the second moving member 62, and a pressing portion 79 capable of pressing the gasket 22 (see FIG. 1). The tip surface of the first moving member 61 constitutes the pressing portion 79. The first tubular body portion 67 has a tip opening and a proximal end opening. The first lumen 61*a* is formed between the tip opening and the proximal end opening.

The first projection portion 68 protrudes radially outward from the outer peripheral surface of the proximal end portion of the first tubular body portion 67. A plurality of (two in the illustrated example) the first projection portions 68 is provided at intervals in the circumferential direction. The plurality of first projection portions 68 is provided at intervals in the circumferential direction and provided at different positions in the axial direction of the first moving member 61 so as to be disposed on a spiral having the same shape as the spiral shape of the screw portion 66. It should be noted that only one first projection portion 68 may be provided as well.

The engagement groove portion 69 is provided in the vicinity of the proximal end of the first tubular body portion 67. A guide groove 70 extending in the axial direction is provided in the inner peripheral surface of the first tubular body portion 67, and the engagement groove portion 69 is provided in the proximal end portion of the guide groove 70. The engagement groove portion 69 in the illustrated example is a through hole penetrating the peripheral wall portion of the first tubular body portion 67 in the thickness direction.

Alternatively, the engagement groove portion 69 may be a bottomed hole (recessed portion) open to the first lumen 61*a* and having a depth toward the radially outer side of the first tubular body portion 67. In the first moving member 61, a plurality of (two in the illustrated example) the engagement groove portions 69 is provided at intervals in the circumferential direction. Incidentally, although only one engagement groove portion 69 may be provided as well, it is preferable that the plurality of engagement groove portions 69 is provided at equal intervals in the circumferential direction. In the first moving member 61, a plurality of (two in the illustrated example) the guide grooves 70 is provided at intervals in the circumferential direction. Incidentally, although only one guide groove 70 may be provided as well, it is preferable that the plurality of guide grooves 70 is provided at equal intervals in the circumferential direction.

The second moving member 62 is formed of a hollow tubular body having a second lumen 62*a* and is disposed inside the first moving member 61. The second moving member 62 is capable of advancing with respect to the rotation member 60 and the support member 63. The second moving member 62 has a second tubular body portion 71 formed in a hollow cylindrical shape, a second projection portion 72 engageable with the screw portion 66 of the rotation member 60, and the claw portion 73 (second engagement portion) engageable with the engagement groove portion 69 of the first moving member 61. The second tubular body portion 71 has a tip opening and a proximal end opening. The second lumen 62a is formed between the tip opening and the proximal end opening.

The second projection portion 72 protrudes radially outward from the outer peripheral surface of the proximal end portion of the second tubular body portion 71. A plurality of (two in the illustrated example) the second projection portions 72 is provided at intervals in the circumferential direction. The plurality of second projection portions 72 is provided at intervals in the circumferential direction and provided at different positions in the axial direction of the second moving member 62 so as to be disposed on a spiral having the same shape as the spiral shape of the screw portion 66. It should be noted that only one second projection portion 72 may be provided as well.

A guide projection 74 inserted in a guide rail 82 (described later) of the support member 63 is provided on the proximal end portion inner periphery of the second tubular body portion 71. In the second moving member 62 in the illustrated example, a plurality of (two in the illustrated example) the guide projections 74 is provided at intervals in the circumferential direction. Incidentally, although only one guide projection 74 may be provided as well, it is preferable that the plurality of guide projections 74 is provided at equal intervals in the circumferential direction.

The claw portion 73 is elastically supported. Specifically, the claw portion 73 protrudes outward from the tip of an elastic piece 76 elastically deformable in the inward-outward direction (radial direction) of the second moving member 62. The claw portion 73 is engageable with the engagement groove portion 69 of the first moving member 61. The elastic piece 76 is provided on the tip side of the second tubular body portion 71. Two parallel slits 75 open in the tip direction and penetrating the second tubular body portion 71 in the thickness direction of the second tubular body portion 71 are formed in the second tubular body portion 71. The elastic piece 76 is formed between the two slits 75.

In the second moving member 62, a plurality of (two in the illustrated example) the elastic pieces 76 is provided at intervals in the circumferential direction. Incidentally, only one elastic piece 76 may be provided as well. The claw portion 73 is inserted in the guide groove 70 of the first moving member 61. As a result, the first moving member 61 can be displaced in the axial direction with respect to the second moving member 62 with rotation about the axis with respect to the second moving member 62 restricted. Incidentally, it is preferable that the plurality of elastic pieces 76 having the claw portions 73 is provided at equal intervals in the circumferential direction so as to correspond to the guide grooves 70 and the engagement groove portions 69 of the first moving member 61. As a result, inclination of the first moving member 61 with respect to the second moving member 62 is suppressed.

Further, a protruding portion 77 protruding inward is provided at the tip of the claw portion 73. In the initial state of the plunger mechanism 14C, the protruding portion 77 is close to or engaged with a small projection 84 and is closer to the proximal end side than the small projection 84 (described later) of the support member 63. As a result, the second moving member 62 is restricted (temporarily fixed) such that advancing with respect to the support member 63 can be released. Once a predetermined or more force in the tip direction is applied to the second moving member 62, the protruding portion 77 climbs over the small projection 84, and the second moving member 62 advances by means of the force in the tip direction.

The support member 63 has a base portion 80 fixed to the inner surface of the housing 25 (see FIG. 1) and a support shaft portion 81 extending in the tip direction from the base portion 80. The support shaft portion 81 is formed in a hollow cylindrical shape. The support shaft portion 81 is inserted in the second lumen 62a of the second moving member 62. The recessed guide rail 82 is provided along the axial direction of the support shaft portion 81 in the outside portion of the support shaft portion 81.

The guide projection 74 of the second moving member 62 is inserted in the guide rail 82. As a result, the second moving member 62 can be displaced in the axial direction with respect to the rotation member 60 and the support member 63 with rotation about the axis restricted. In the support shaft portion 81, a plurality of (two in the illustrated example) the guide rails 82 is provided (see FIG. 15). Incidentally, although only one guide rail 82 may be provided as well, it is preferable that the plurality of guide rails 82 is provided at equal intervals in the circumferential direction so as to correspond to the guide projections 74 of the second moving member 62. As a result, inclination of the second moving member 62 with respect to the support member 63 is suppressed.

The tip region of each guide rail 82 is a slit 82a open in the tip direction and penetrating the peripheral wall of the support shaft portion 81 in the thickness direction. The slit 82a is provided with an elastic piece 83 extending in the tip direction from the proximal end of the slit 82a. The elastic piece 83 is elastically deformable in the radial direction of the support shaft portion 81. The small projection 84 bulging outward is provided at the tip (free end) of the elastic piece 83. The small projection 84 constitutes a temporary fixing mechanism that temporarily fixes the second moving member 62 to the support member 63 together with the above-described protruding portion 77 of the second moving member 62.

Figure 15:
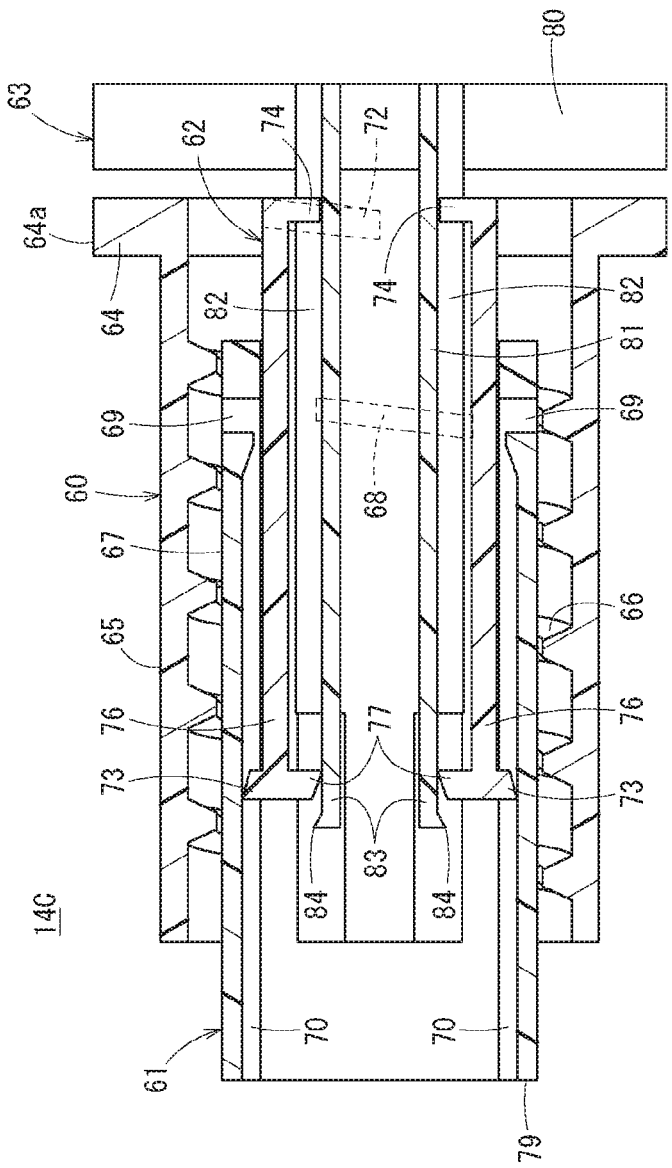
FIG. 15 is a cross-sectional view of the initial state of the plunger mechanism illustrated in FIG. 13.

As illustrated in FIG. 15, each portion of the plunger mechanism 14C is as follows in the initial state of the plunger mechanism 14C. The rotation member 60, the first moving member 61, and the second moving member 62 are disposed at positions overlapping each other in the axial direction. The screw portion 66 of the rotation member 60 and the first projection portion 68 of the first moving member 61 are engaged. The screw portion 66 of the rotation member 60 and the second projection portion 72 of the second moving member 62 are not engaged. The claw portion 73 (first engagement portion) and the engagement groove portion 69 (second engagement portion) are not engaged. The protruding portion 77 of the second moving member 62 and the small projection 84 of the support member 63 are close to or engaged with each other.

Once the drive unit 23 illustrated in FIG. 1 starts operating, the plunger mechanism 14C extends in a plurality of stages under the drive action of the drive unit 23. Specifically, the extension operation of the plunger mechanism 14C has a first extension operation and a second extension operation subsequent to the first extension operation as described below.

Figure 16:
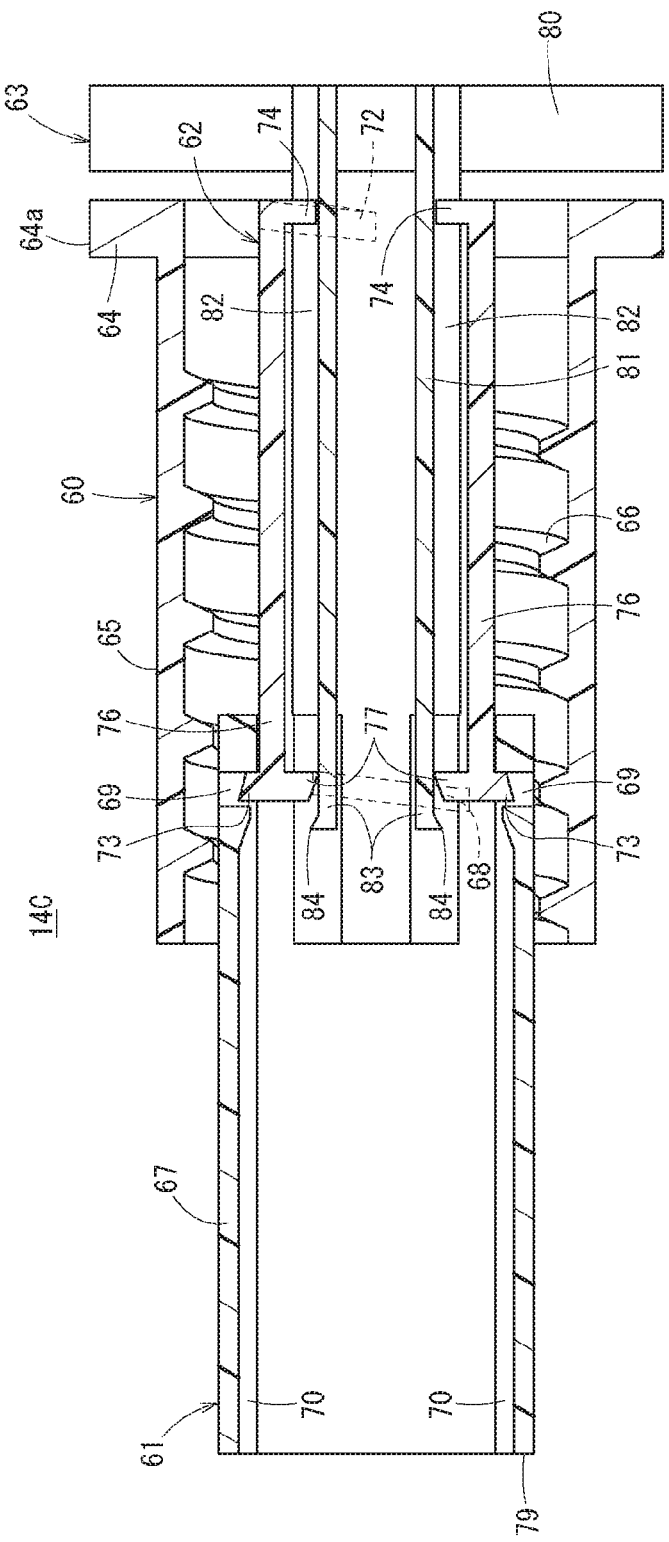
FIG. 16 is a cross-sectional view of a state in which a first moving member has advanced with respect to a second moving member in the plunger mechanism illustrated in FIG. 13.

In the first extension operation, the rotation member 60 rotates from the initial state. As illustrated in FIG. 16, in conjunction with this rotation and under the engagement action of the screw portion 66 and the first projection portion 68, the first moving member 61 advances to a predetermined position with respect to the rotation member 60 and the second moving member 62. In this case, rotation of the first moving member 61 about the axis relative to the second moving member 62 is restricted and rotation of the second moving member 62 about the axis relative to the support member 63 is restricted, and thus the first moving member 61 does not rotate along with the rotation of the rotation member 60. In other words, the first projection portion 68 does not rotate. Accordingly, the first projection portion 68 is sent in the tip direction by the rotating screw portion 66. As a result, the first moving member 61 advances. At this time, there is some frictional resistance between the first moving member 61 and the second moving member 62, and thus the first moving member 61 pulls the second moving member 62 in the tip direction with a weak force. However, this pulling force is smaller than the force that is required for the protruding portion 77 of the second moving member 62 to climb over the small projection 84 of the support member 63. As a result, it is possible to prevent the second moving member 62 from advancing by being pulled by the advancing of the first moving member 61 during the first extension operation.

Further, as illustrated in FIG. 16, the claw portion 73 and the engagement groove portion 69 are engaged when the first moving member 61 has advanced to the predetermined position with respect to the second moving member 62 by the rotation of the rotation member 60. As a result, a state occurs where axial displacement of the first moving member 61 relative to the second moving member 62 is restricted. In this manner, the claw portion 73 and the engagement groove portion 69 can be quickly engaged at a point in time when the first moving member 61 has advanced to the maximum with respect to the second moving member 62, and thus the first moving member 61 can be swiftly locked with respect to the second moving member 62 through a linear movement alone.

In the state that is illustrated in FIG. 16, the engagement between the screw portion 66 and the first projection portion 68 is maintained. Accordingly, once the rotation member 60 further rotates from the state illustrated in FIG. 16, the first moving member 61 further advances under the engagement action of the screw portion 66 and the first projection portion 68 as illustrated in FIGS. 17A and 17B. At this time, the claw portion 73 and the engagement groove portion 69 are engaged, and thus the second moving member 62 advances together with the first moving member 61 by being pulled in the tip direction by the first moving member 61. The force with which the first moving member 61 pulls the second moving member 62 in the tip direction in a state in which the claw portion 73 and the engagement groove portion 69 are engaged is larger than the engagement force of the protruding portion 77 of the second moving member 62 and the small projection 84 of the support member 63. Accordingly, once the second moving member 62 further advances from the state that is illustrated in FIG. 17A, the protruding portion 77 climbs over the small projection 84, and the engagement between the protruding portion 77 and the small projection 84 is released as a result. Incidentally, as illustrated in FIG. 17B, at this point in time, the screw portion 66 and the second projection portion 72 are yet to be engaged.

When the first moving member 61 and the second moving member 62 further advance as the rotation member 60 further rotates from the state illustrated in FIGS. 17A and 17B, engagement between the screw portion 66 and the second projection portion 72 is initiated and the screw portion 66 and the first projection portion 68 are disengaged as illustrated in FIGS. 18A and 18B. Specifically, the screw portion 66 and the first projection portion 68 are disengaged after the screw portion 66 and the second projection portion 72 are engaged. With this configuration, the engagement opponent of the screw portion 66 can be timely changed from the first projection portion 68 to the second projection portion 72, and thus a transition from the first extension operation to the second extension operation can be smoothly performed.

Figure 19:
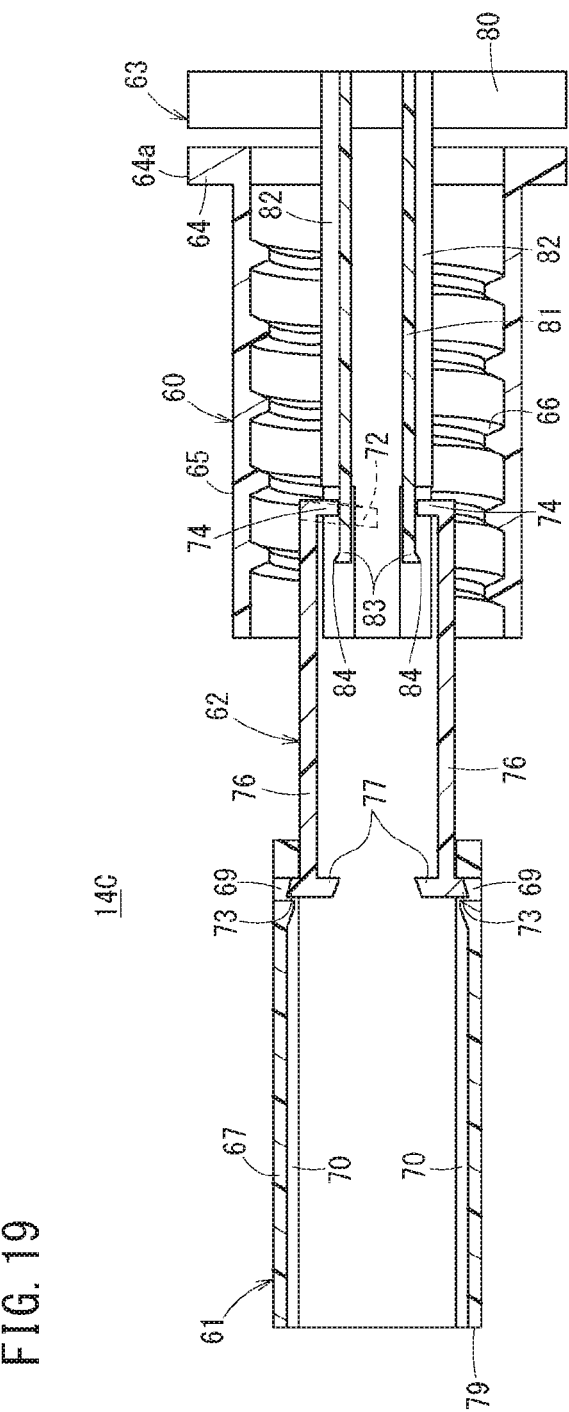
FIG. 19 is a cross-sectional view of a state in which an extension operation of the plunger mechanism illustrated in FIG. 13 is completed.

Next, in the second extension operation of the plunger mechanism 14C, the rotation member 60 further rotates from the state illustrated in FIGS. 18A and 18B. As illustrated in FIG. 19, in conjunction with this rotation and under the engagement action of the screw portion 66 and the second projection portion 72, the second moving member 62 advances with respect to the rotation member 60 together with the first moving member 61. At this time, the engagement between the screw portion 66 and the first projection portion 68 is released, and thus the first moving member 61 is not directly driven by the rotation member 60. However, the claw portion 73 and the engagement groove portion 69 are engaged, and thus the first moving member 61 is pressed in the tip direction by the second moving member 62 to advance together with the second moving member 62. Subsequently, the first moving member 61 and the second moving member 62 stop advancing when the gasket 22 (see FIG. 1) reaches the most distal position in the movable range (when the gasket 22 abuts against the shoulder portion 12b of the barrel 12). In other words, the extension of the plunger mechanism 14C is completed.

Incidentally, although the barrel 12, the gasket 22, and the drug solution M are not illustrated in FIGS. 15 to 19, the drug solution M is discharged from the barrel 12 by the gasket 22 being pressed by the pressing portion 79 and advancing in the barrel 12 as the first moving member 61 advances, which is similar to a case where the plunger mechanism 14A is operated.

As described above, the plunger mechanism 14C extends over a plurality of stages, and thus it is possible to shorten the plunger mechanism 14C and the drug solution injection device 10 (see FIG. 1) can be reduced in size to the same extent as in the case of the plunger mechanism 14A described above.

Figure 20:
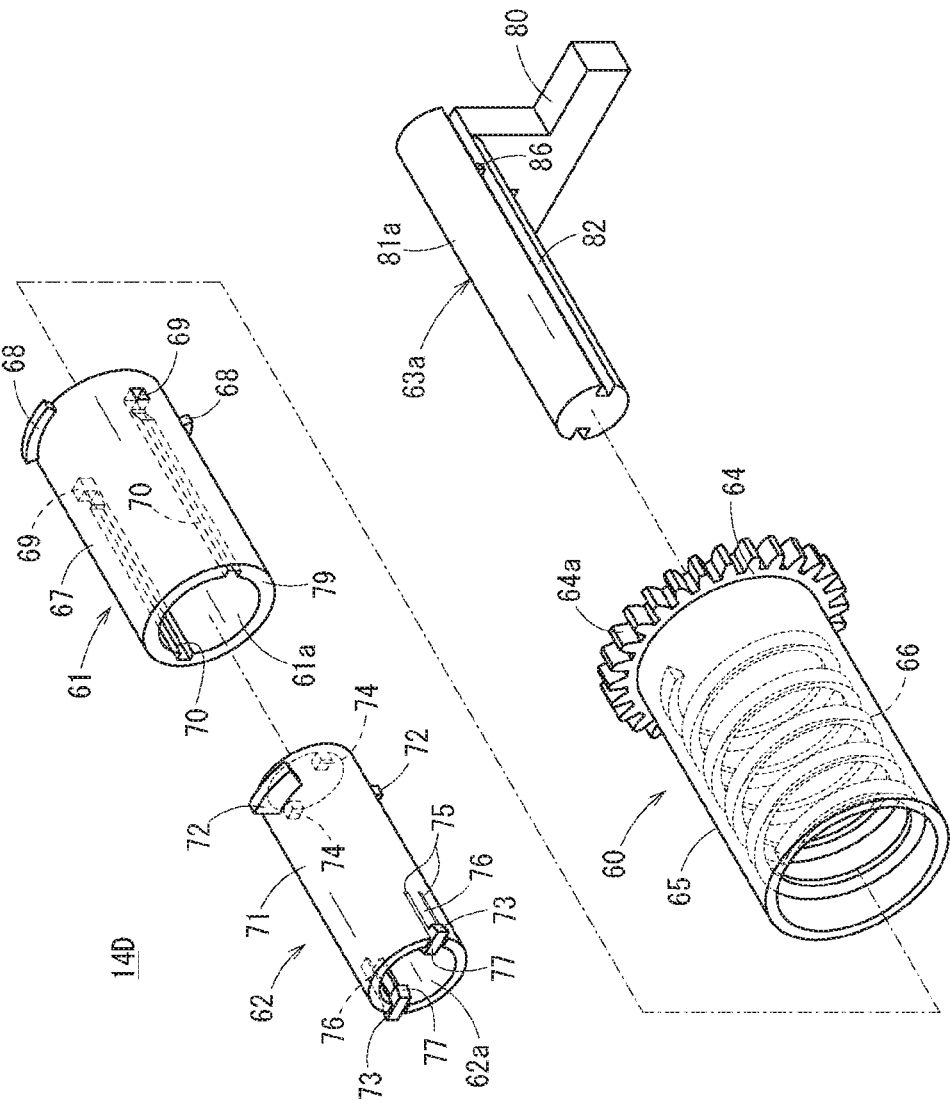
FIG. 20 is an exploded perspective view of a plunger mechanism according to a fourth configuration example.

The plunger mechanism 14D according to the fourth modification example illustrated in FIG. 20 differs from the plunger mechanism 14C according to the third configuration example in terms of the configuration of a support member 63a.

The support member 63a has a locking projection 86 (see also FIG. 21) protruding outward from the bottom portion of the guide rail 82. The locking projection 86 is provided on the proximal end side of the guide rail 82. A plurality of (two in the illustrated example) the locking projections 86 is provided at intervals in the circumferential direction. Only one locking projection 86 may be provided as well. Incidentally, unlike in the support member 63 (see FIG. 14) according to the third configuration example, a support shaft portion 81a protruding in the tip direction from the base portion 80 has a solid structure and the slit 82a and the elastic piece 83 are not provided in the tip portion of the support shaft portion 81a.

Figure 21:
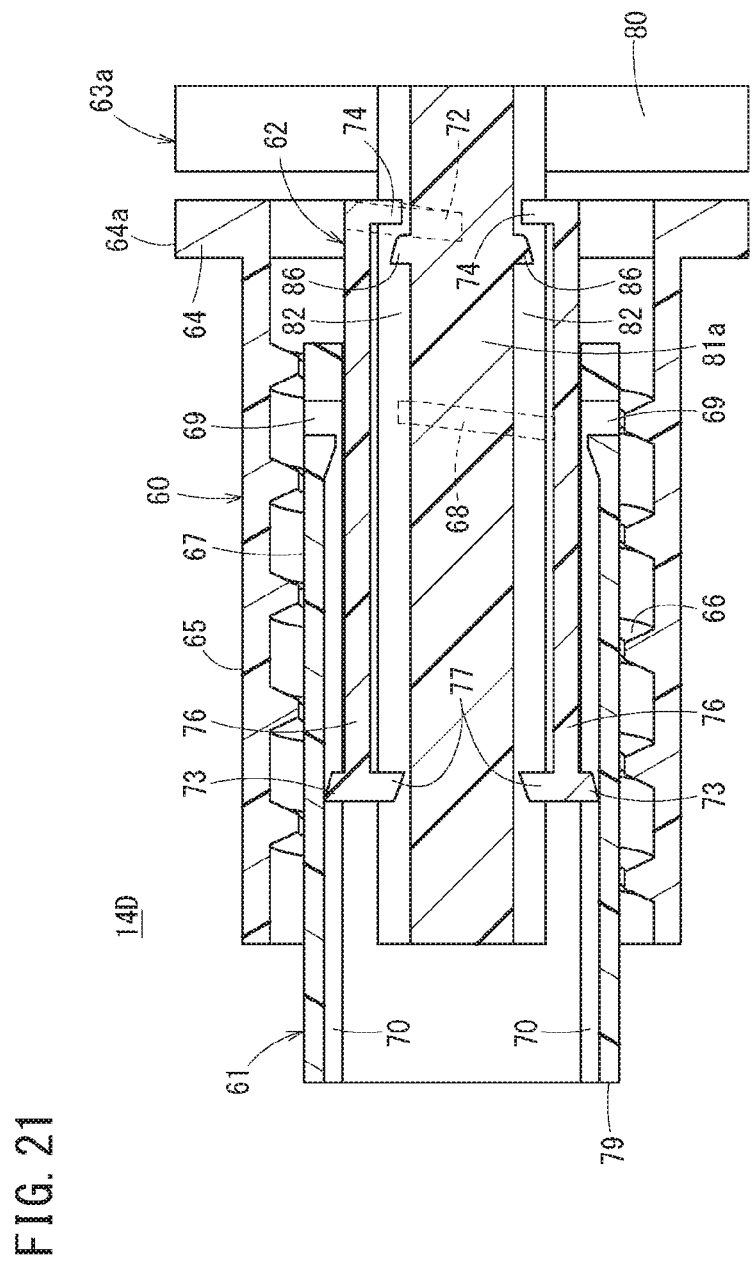
FIG. 21 is a cross-sectional view of an initial state of the plunger mechanism illustrated in FIG. 20.

In the initial state of the plunger mechanism 14D illustrated in FIG. 21, the guide projection 74 is close to or engaged with the locking projection 86 and is closer to the proximal end side than the locking projection 86. As a result, the second moving member 62 is releasably restricted (temporarily fixed) so as not to advance with respect to the support member 63a. Once a predetermined or more force in the tip direction is applied to the second moving member 62, the guide projection 74 climbs over the locking projection 86, and the second moving member 62 advances by means of the force in the tip direction. In this manner, the guide projection 74 and the locking projection 86 constitute a temporary fixing mechanism that releasably restricts the second moving member 62 so as not to advance with respect to the support member 63a.

Once the rotation member 60 rotates from the initial state illustrated in FIG. 21, the first moving member 61 advances under the engagement action of the screw portion 66 and the first projection portion 68, and the plunger mechanism 14D extends as a result (first extension operation). Although the first moving member 61 pulls the second moving member 62 in the tip direction with a weak force at this time, this pulling force is smaller than the force that is required for the guide projection 74 of the second moving member 62 to climb over the locking projection 86 of the support member 63a. As a result, it is possible to prevent the second moving member 62 from advancing by being pulled by the advancing of the first moving member 61 during the first extension operation.

Figure 22:
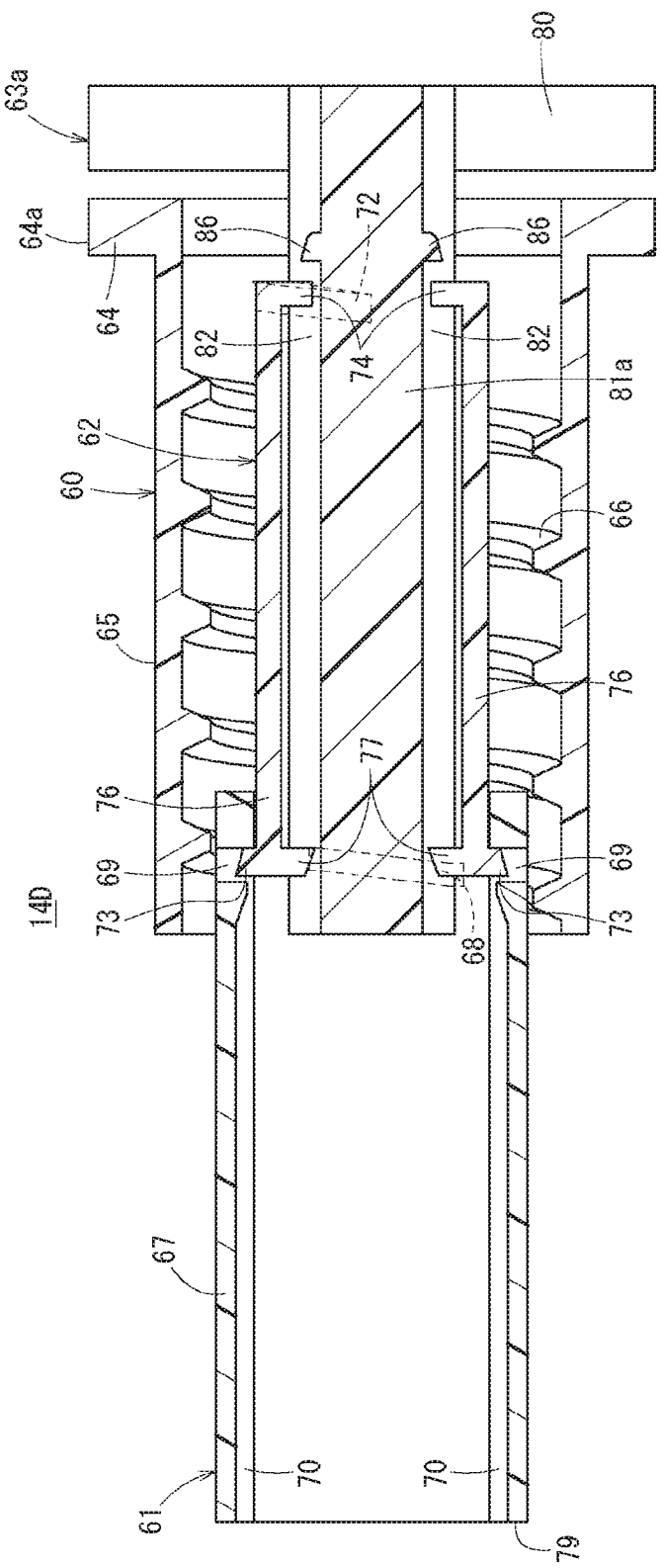
FIG. 22 is a cross-sectional view of a state in which a guide projection and a locking projection are disengaged in the plunger mechanism illustrated in FIG. 20.

The claw portion 73 and the engagement groove portion 69 are engaged when the first moving member 61 has advanced to a predetermined position with respect to the second moving member 62 by the rotation of the rotation member 60. As a result, a state occurs where axial displacement of the first moving member 61 relative to the second moving member 62 is restricted. Then, the first moving member 61 further advances once the rotation member 60 further rotates from this state. At this time, the claw portion 73 and the engagement groove portion 69 are engaged as illustrated in FIG. 22, and thus the second moving member 62 advances together with the first moving member 61 by being pulled in the tip direction by the first moving member 61. The force with which the first moving member 61 pulls the second moving member 62 in the tip direction in a state in which the claw portion 73 and the engagement groove portion 69 are engaged is larger than the engagement force of the guide projection 74 of the second moving member 62 and the locking projection 86 of the support member 63a. Accordingly, the guide projection 74 and the locking projection 86 are disengaged by the guide projection 74 climbing over the locking projection 86 as illustrated in FIG. 22.

The subsequent operation of the plunger mechanism 14D is similar to the operation of the plunger mechanism 14C according to the third configuration example described above. Although the barrel 12, the gasket 22, and the drug solution M are not illustrated in FIGS. 20 to 22, the drug solution M is discharged from the barrel 12 by the gasket 22 being pressed by the pressing portion 79 and advancing in the barrel 12 as the first moving member 61 advances, which is similar to a case where the plunger mechanism 14A is operated.

Incidentally, the plunger mechanism 14D is identical or similar in action and effect to the plunger mechanism 14C when it comes to the parts of the plunger mechanism 14D according to the fourth configuration example that are the same as those of the plunger mechanism 14C according to the third configuration example.

Figure 23:
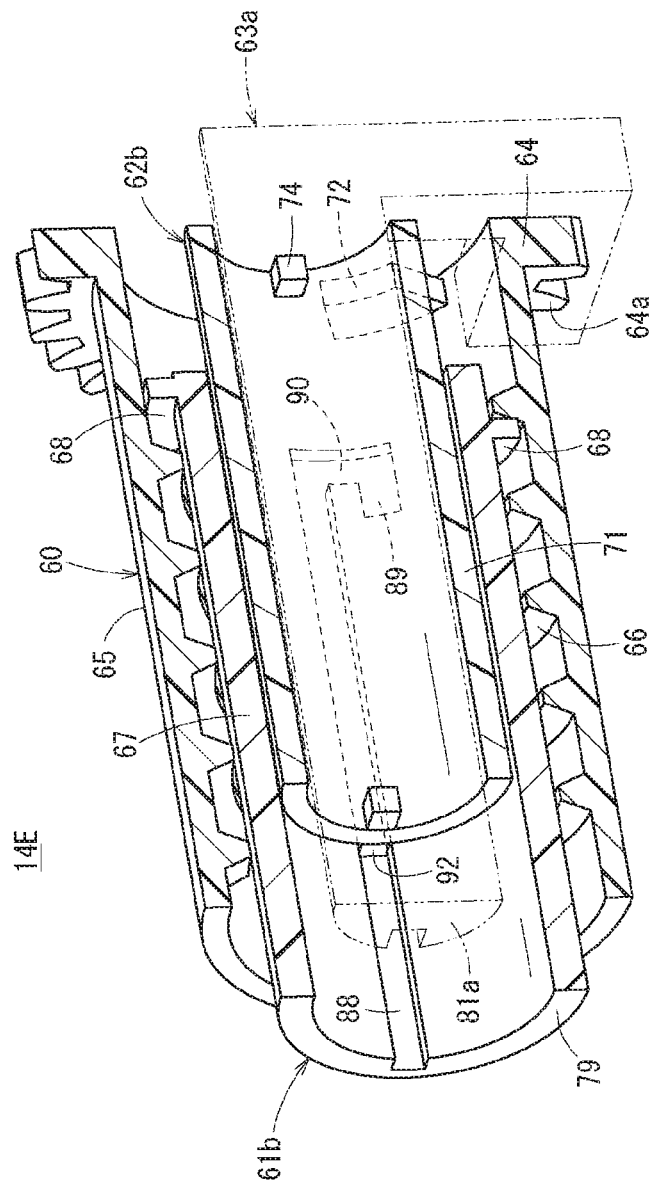
FIG. 23 is a perspective cross-sectional view of an initial state of a plunger mechanism according to a fifth configuration example.

The plunger mechanism 14E according to the fifth configuration example illustrated in FIG. 23 differs from the plunger mechanism 14C according to the third configuration example in terms of the configurations of a first moving member 61b, a second moving member 62b, and the support member 63a.

The inner peripheral portion of the first moving member 61b is provided with a guide groove 88 extending in the axial direction, a lock groove 89 (first engagement portion) shorter than the guide groove 88, and a relay groove 90 connecting one end (proximal end) of the guide groove 88 and one end (proximal end) of the lock groove 89. The lock groove 89 communicates with the guide groove 88 via the relay groove 90, extends in the tip direction from the relay groove 90, and slightly extends in the tip direction from the end portion of the relay groove 90 on the side opposite to the guide groove 88. Accordingly, the tip of the lock groove 89 is closer to the proximal end side than the tip of the guide groove 88. The lock groove 89 extends in parallel to the guide groove 88. The extension length of the lock groove 89 from the relay groove 90 may be approximately equal to the length of a projecting portion 92 along the axial direction of the second moving member 62b or may be shorter than the length of the projecting portion 92. The relay groove 90 extends in the circumferential direction of the first moving member 61b.

In the first moving member 61b, two groove structures are line-symmetrically provided with respect to the central axis of the second moving member 62b and the guide groove 88, the relay groove 90, and the lock groove 89 constitute each of the groove structures. Although only one groove structure may be provided as well, it is preferable that a plurality of the groove structures is provided at equal intervals in the circumferential direction.

The second moving member 62b has the projecting portion 92 (second engagement portion) protruding outward from the proximal end portion outer surface of the second tubular body portion 71. The projecting portion 92 is engageable with the lock groove 89 of the first moving member 61b. A plurality of (two in the illustrated example) the projecting portions 92 is provided at intervals in the circumferential direction. Only one projecting portion 92 may be provided in a case where only one groove mechanism is provided in the second moving member 62b. Still, it is preferable that the plurality of projecting portions 92 is provided at equal intervals in the circumferential direction. As a result, inclination of the first moving member 61b with respect to the second moving member 62b is suppressed. Further, as in the case of the second moving member 62 of the plunger mechanism 14C, the guide projection 74 is provided in the proximal end inner peripheral portion of the second moving member 62b.

The support member 63a is similar in configuration to the support member 63a of the plunger mechanism 14D according to the fourth configuration example.

Incidentally, the other parts of the plunger mechanism 14E are similar in configuration to plunger mechanism 14C according to the third configuration example described above.

As illustrated in FIG. 23, in the initial state of the plunger mechanism 14E, the projecting portion 92 is inserted in the guide groove 88. Once the rotation member 60 rotates in the arrow A direction from the state illustrated in FIG. 23, the first moving member 61b advances under the engagement action of the screw portion 66 and the first projection portion 68, and the plunger mechanism 14E extends as a result (first extension operation). At this time, the projecting portion 92 relatively retreats with respect to the guide groove 88. As the first moving member 61b advances, the projecting portion 92 reaches the most proximal portion of the guide groove 88 (place where the guide groove 88 and the relay groove 90 are connected). Then, the projecting portion 92 enters the lock groove 89 via the relay groove 90. As a result, a movement of the first moving member 61b in the proximal end direction relative to the second moving member 62b is restricted (locked).

Specifically, the lock operation restricting a movement of the first moving member 61b in the proximal end direction relative to the second moving member 62b in the plunger mechanism 14E has a rotation operation (FIG. 24) as a first lock operation and a locking operation (FIG. 25) as a second lock operation subsequent to the rotation operation.

Figure 24:
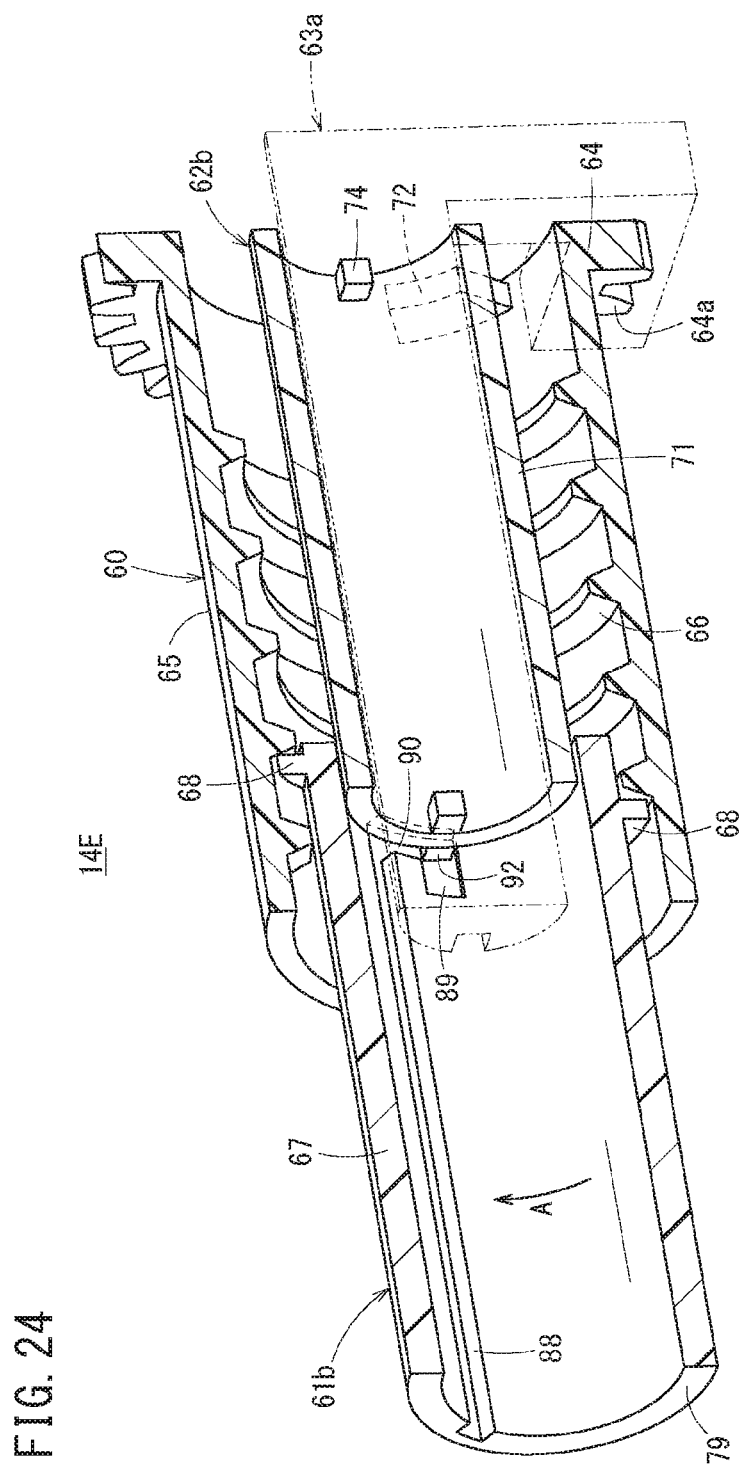
FIG. 24 is a perspective cross-sectional view illustrating a rotation operation of a lock operation of the plunger mechanism illustrated in FIG. 23.

In the rotation operation, the first moving member 61b rotates in the arrow B direction with respect to the second moving member 62b as illustrated in FIG. 24 after the projecting portion 92 reaches the proximal end portion of the guide groove 88 as described above. As a result, the projecting portion 92 relatively moves in the relay groove 90 toward the lock groove 89. In other words, the projecting portion 92 moves in the circumferential direction in the relay groove 90. When the projecting portion 92 reaches the proximal end portion of the guide groove 88, restriction on rotation of the first moving member 61b relative to the second moving member 62b is released. Accordingly, rotation of the first moving member 61b in the arrow B direction is performed as described above by the rotational force that the first moving member 61b receives from the rotating rotation member 60. As a result, the projecting portion 92 reaches the end portion of the relay groove 90 on the lock groove 89 side.

Figure 25:
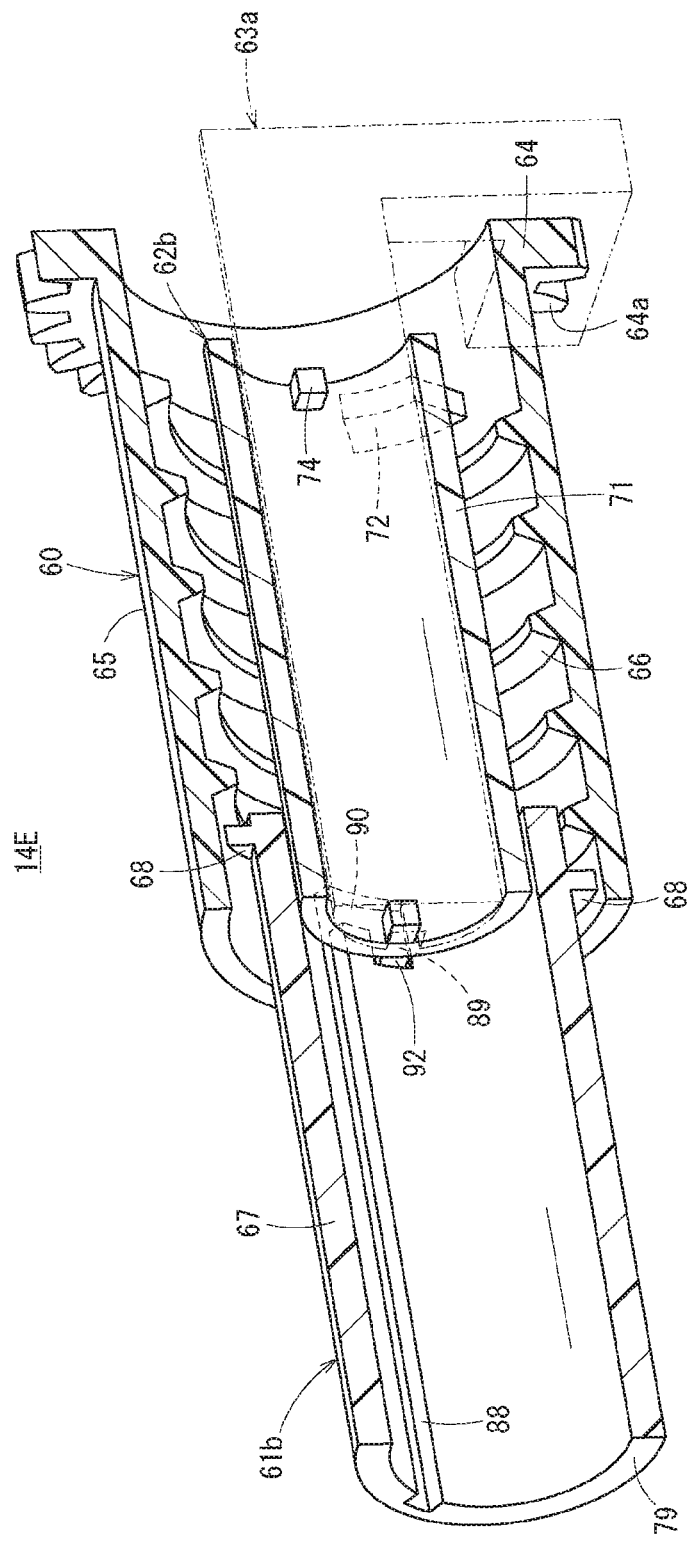
FIG. 25 is a perspective cross-sectional view illustrating a locking operation of the lock operation of the plunger mechanism illustrated in FIG. 23.

Next, in the locking operation, the projecting portion 92 enters the lock groove 89 and the projecting portion 92 is locked in the lock groove 89 by the second moving member 62b advancing with respect to the first moving member 61b as illustrated in FIG. 25. This locking operation is performed after the screw portion 66 of the rotation member 60 and the second projection portion 72 of the second moving member 62b are engaged and the screw portion 66 and the first projection portion 68 of the first moving member 61b are disengaged. Once the rotation member 60 rotates in a state in which the screw portion 66 and the first projection portion 68 of the first moving member 61b are disengaged and the projecting portion 92 is positioned in the end portion of the relay groove 90 on the lock groove 89 side, the second moving member 62b advances under the engagement action of the screw portion 66 and the second projection portion 72.

In the initial stage of the advancing of the second moving member 62b, only the second moving member 62b advances with the first moving member 61b stopped. In other words, the projecting portion 92 enters the lock groove 89 by the first moving member 61b relatively retreating with respect to the second moving member 62b. Then, the projecting portion 92 is locked by the lock groove 89 by the projecting portion 92 abutting against the proximal end side wall of the lock groove 89. In a state in which the projecting portion 92 is locked by the lock groove 89, a movement of the first moving member 61b in the proximal end direction relative to the second moving member 62b is blocked. Accordingly, after the locking operation is completed, the first moving member 61b advances together with the second moving member 62b as the rotation member 60 rotates. By the second moving member 62b advancing together with the first moving member 61b in this manner, the plunger mechanism 14E further extends (second extension operation).

Incidentally, although the barrel 12, the gasket 22, and the drug solution M are not illustrated in FIGS. 23 to 25, the drug solution M is discharged from the barrel 12 by the gasket 22 being pressed by the pressing portion 79 and advancing in the barrel 12 as the first moving member 61b advances, which is similar to a case where the plunger mechanism 14A is operated.

In the plunger mechanism 14E configured as described above, the projecting portion 92 is provided on the outer surface of the second moving member 62b (outer surface of the second tubular body portion 71). Accordingly, the projecting portion 92 is capable of having higher strength than the claw portion 73 provided in the second moving member 62 of the plunger mechanism 14C described above. Accordingly, it is possible to structurally stabilize the mechanism portion that locks the first moving member 61b with respect to the second moving member 62b.

Incidentally, the plunger mechanism 14E is identical or similar in action and effect to the plunger mechanism 14C when it comes to the parts of the plunger mechanism 14E according to the fifth configuration example that are the same as those of the plunger mechanism 14C according to the third configuration example.

The present invention is not limited to the above-described embodiments, and various modifications are possible without departing from the gist of the present invention.

What is claimed is:

1. A drug solution injection device for injecting a drug solution into a living body, comprising:
   a barrel filled with the drug solution;
   a gasket slidably disposed in the barrel; and
   a plunger mechanism that is configured to extend in an axial direction and to push out the drug solution from the barrel by pressing the gasket as the plunger mechanism extends, wherein the plunger mechanism comprises:
   a rotatable rotation member comprising a screw portion,
   a first moving member comprising a first projection portion that is configured to engage with the screw portion, and a pressing portion that is configured to press the gasket, the first moving member being configured to be displaced in the axial direction with respect to the rotation member, and
   a second moving member comprising a second projection portion that is configured to engage with the screw portion, the second moving member being configured to be displaced in the axial direction with respect to the rotation member,
   wherein the drug solution injection device is configured such that, in an initial state in which the drug solution is yet to be pushed out:
   the rotation member, the first moving member and the second moving member are disposed at positions overlapping each other in the axial direction,
   the screw portion and the first projection portion are engaged with each other, and
   the screw portion and the second projection portion are not engaged with each other, and
   wherein the plunger mechanism is configured to perform:
   a first extension operation, in which, as the rotation member rotates from the initial state, the first moving member advances to a predetermined position with respect to the rotation member and the second moving member due to engagement of the screw portion with the first projection portion; and
   a second extension operation, in which, in conjunction with a rotation of the rotation member after the first extension operation, the second moving member advances with respect to the rotation member together with the first moving member due to engagement of the screw portion with the second projection portion.

2. The drug solution injection device according to claim 1, wherein:
   the first moving member comprises a first engagement portion;

the second moving member comprises a second engagement portion configured to engage with the first engagement portion; and when the first moving member has advanced to the predetermined position with respect to the second moving member, the first engagement portion and the second engagement portion are engaged with each other such that axial displacement of the first moving member relative to the second moving member is restricted.

3. The drug solution injection device according to claim 2, wherein:

one of the first engagement portion and the second engagement portion is an elastically supported claw portion; and the other of the first engagement portion and the second engagement portion is an engagement groove portion with which the claw portion is configured to engage.

4. The drug solution injection device according to claim 2, wherein:

one member among the first moving member and the second moving member includes a guide groove extending along the axial direction of the plunger mechanism;

the engagement portion of an other member among the first moving member and the second moving member is a projecting portion that protrudes from an outer surface or an inner surface of said other member and that is configured to be inserted into the guide groove in the initial state;

the engagement portion of said one member is a lock groove that is shorter than the guide groove and that is configured to engage with the projecting portion;

the lock groove and the projecting portion are configured such that movement of the first moving member in a proximal end direction relative to the second moving member is restricted by engagement between the lock groove and the projecting portion;

the lock groove is disposed at a different circumferential position from the guide groove in said one member;

one end of the guide groove and one end of the lock groove communicate with each other via a relay groove; and the plunger mechanism is configured to perform a lock operation that restricts the movement of the first moving member in the proximal end direction relative to the second moving member, the lock operation comprising:

a rotation operation in which, in conjunction with an advancement of the first moving member with respect to the second moving member, the first moving member rotates with respect to the second moving member after the projecting portion relatively moves in the axial direction with respect to the guide groove, such that the projecting portion relatively moves in the relay groove toward the lock groove; and a locking operation in which, after the rotation operation, the second moving member advances with respect to the first moving member, such that the projecting portion enters the lock groove and the projecting portion is locked in the lock groove.

5. The drug solution injection device according to claim 1, wherein:

the screw portion and the first projection portion are configured to be disengaged after the screw portion and the second projection portion are engaged with each other in conjunction with a rotation of the rotation member during the second extension operation.

6. The drug solution injection device according to claim 1, wherein:

the screw portion comprises a male screw;

the first moving member comprises a hollow tubular body including a first lumen;

the first projection portion protrudes toward an inside of the first moving member;

in the initial state, the male screw is inserted in the first lumen; and the second moving member comprises a hollow tubular body including a second lumen;

the second projection portion protrudes toward an inside of the second moving member; and the male screw and the first moving member are configured to be inserted in the second lumen.

7. The drug solution injection device according to claim 1, wherein:

the rotation member comprises a hollow tubular body including a lumen;

the screw portion comprises a female screw formed in an inner peripheral portion of the rotation member;

the first moving member comprises a hollow tubular body including a first lumen;

the first projection portion protrudes toward an outside of the first moving member;

in the initial state, the first moving member is inserted in the lumen;

the second projection portion protrudes toward an outside of the second moving member; and the second moving member is configured to be inserted in the first lumen.

8. The drug solution injection device according to claim 1, further comprising:

a support member that is configured to guide the second moving member in the axial direction while restricting rotation of the second moving member;

wherein the second moving member comprises a guide portion that is configured to guide the first moving member in the axial direction while restricting rotation of the first moving member.

9. The drug solution injection device according to claim 1, further comprising:

a support member that is configured to guide the second moving member in the axial direction, wherein:

the support member and the second moving member are configured to engage with each other such that the position of the second moving member with respect to the rotation member is maintained until termination of the first extension operation; and the rotation member is configured to rotate, with the screw portion and the first projection portion engaged with each other, such that the support member and the second moving member are disengaged.

* * * * *